(12) United States Patent
Wang et al.

(10) Patent No.: US 10,442,835 B2
(45) Date of Patent: Oct. 15, 2019

(54) WATER-SOLUBLE RAPAMYCIN DERIVATIVES

(71) Applicant: Zhejiang Hisun Pharmaceutical Co., Ltd., Taizhou (CN)

(72) Inventors: Haibo Wang, Taizhou (CN); Hongfu Kuang, Taizhou (CN); Wei Zhang, Taizhou (CN); Zhengjiang Cai, Taizhou (CN); Tianmin Zhu, Taizhou (CN); Xiaohe Zheng, Taizhou (CN); Zhongwei Wu, Taizhou (CN); Zhiqing Yang, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 15/553,088

(22) PCT Filed: Nov. 9, 2016

(86) PCT No.: PCT/CN2016/105178
§ 371 (c)(1),
(2) Date: Aug. 23, 2017

(87) PCT Pub. No.: WO2017/193562
PCT Pub. Date: Nov. 16, 2017

(65) Prior Publication Data
US 2019/0055284 A1   Feb. 21, 2019

(30) Foreign Application Priority Data

May 10, 2016 (CN) .......................... 2016 1 0305510

(51) Int. Cl.
| C07K 5/02 | (2006.01) |
| A61P 35/00 | (2006.01) |
| A61K 38/00 | (2006.01) |

(52) U.S. Cl.
CPC ............ C07K 5/0215 (2013.01); A61P 35/00 (2018.01); A61K 38/00 (2013.01)

(58) Field of Classification Search
CPC .... A61K 38/00; A61K 38/12; C07K 2317/24; C07K 2317/92; C07K 2317/94; C07K 2319/70; C07K 2319/74
See application file for complete search history.

(56) References Cited

U.S. PATENT DOCUMENTS

| 4,284,788 A | 8/1981 | Hohenlohe-Oehringen et al. |
| 9,138,484 B2 | 9/2015 | Leamon et al. |
| 2011/0305751 A1 | 12/2011 | Gaillard |
| 2012/0220580 A1 | 8/2012 | Li et al. |

FOREIGN PATENT DOCUMENTS

| CN | 1823081 A | 8/2006 |
| CN | 101123878 A | 2/2008 |
| CN | 102040569 A | 5/2011 |
| CN | 102316902 A | 1/2012 |
| CN | 102911251 A | 2/2013 |
| CN | 104689330 A | 6/2015 |
| CN | 105461738 A | 4/2016 |
| EP | 0022446 A1 | 1/1981 |
| EP | 3153165 A1 | 4/2017 |
| WO | 0224706 A2 | 3/2002 |
| WO | 2004101583 A1 | 11/2004 |
| WO | 2005046575 A2 | 5/2005 |
| WO | WO2005042567 A1 * | 5/2005 | ............... C07K 7/06 |
| WO | WO2014075554 A1 * | 5/2014 | ........... A61K 31/436 |

OTHER PUBLICATIONS

Tai et al. A novel rapamycin-polymer conjugate based on a new poly(ethylene glycol) multiblock copolyer. Pharm Res. Mar. 2014; 31(3): 706-719. (Year: 2014).*
Paghdal et al. Sirolimus (rapamycin): from the soil of Easter Island to a bright future. J Am Acad Dermatol. Dec. 2007;57(6):1046-50. Epub Jun. 21, 2007. (Year: 2007).*
Wang et al.: "Synthesis and evaluation of an injectable everolimus prodrug", Bioorg. Med. Chem. Lett., vol. 27, No. 5, Jan. 25, 2017, pp. 1175-1178.
European Search Report for Application No. 16901517.9 dated Oct. 4, 2018.

(Continued)

Primary Examiner — Marcela M Cordero Garcia
Assistant Examiner — Jia-Hai Lee
(74) Attorney, Agent, or Firm — Lerner, David, Littenberg, Krumholz & Mentlik, LLP

(57) ABSTRACT

The present invention relates to technical fields of organic chemistry and pharmaceutical chemistry, specifically to water-soluble rapamycin derivatives modified with glutathione. More specifically, the present invention discloses a compound of formula I and the preparation method thereof, wherein $R_1$ and $R_2$ are as defined in the description. The compound of formula I can be used in inducing immunosuppression and in the treatment of diseases such as transplant rejection and solid tumor, etc.

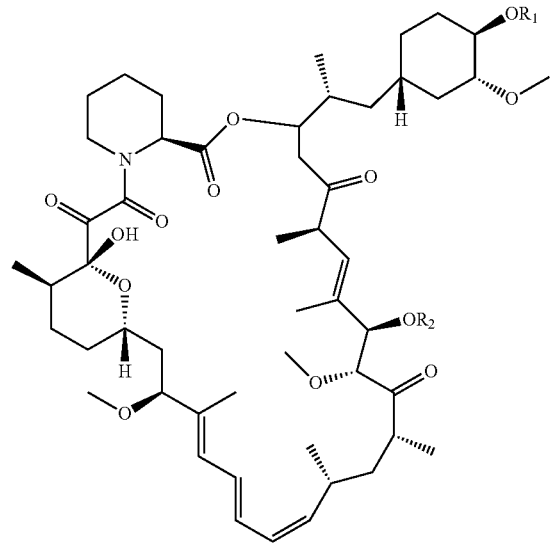

29 Claims, 5 Drawing Sheets

(56) References Cited

OTHER PUBLICATIONS

Guy Jerusalem, et al, "Phase I trial of oral mTOR inhibitor everolimus in combination with trastuzumab and vinorelbine in pre-treated patients with HER2-overexpressing metastatic breast cnacer", Breast Cancer Research and Treatment, 2011, 125:447-455.
Harrison D.E., et al, "Rapamycin fed late in life extends lifespan in genetically heterogeneous mice", Nature, Jul. 16, 2009, 460(7253), 392-395.
International Search Report for Application No. PCT/CN2016/105178 dated Feb. 3, 2017, 7 pages.
Martel et al., "Inhibition of the immune response by rapamycin, a new antifungal antibiotic", Can J. Physiol. Pharmcol. 1977, 55, 48-52.
The FASEB Journal, vol. 3 No. 3, 3411, 1989, 1 page.
Vézina C, et al, "Rapamycin (AY-22,989), A new antifungal antibiotic", The Journal of Antibiotics, vol. XXVIII, No. 10, Oct. 1975, pp. 721-726.

* cited by examiner

WATER-SOLUBLE RAPAMYCIN DERIVATIVES

CROSS REFERENCE TO RELATED APPLICATIONS

The present application is a national phase entry under 35 U.S.C. § 371 of International Application No. PCT/CN2016/105178, filed Nov. 9, 2016, which claims priority from Chinese Patent Application No. 201610305510.9 filed May 10, 2016, all of which are hereby incorporated herein by reference.

FIELD OF THE INVENTION

The present invention relates to technical fields of organic chemistry and pharmaceutical chemistry, specifically to the preparation of water-soluble rapamycin derivatives, and the use thereof in inducing immunosuppression and in the treatment of transplant rejection, solid tumor, fungal infection and vascular disease. More specifically, the present invention relates to a class of water-soluble rapamycin derivatives modified with glutathione, the preparation method thereof, and the use thereof in inducing immunosuppression and in the treatment of transplant rejection, solid tumor, fungal infection and vascular disease.

BACKGROUND OF THE INVENTION

Rapamycins are novel triene macrolide compounds produced by *Streptomyces hygroscopicus* (Vezina C, et al, J. Antibiot, 1975, 10: 721-726.) or *Actinoplane* sp. (Nakao K, et al, EP022446, Nov. 11, 1993). Typical rapamycin compounds mainly include Sirolimus, Everolimus, Temsirolimus and the like, which have the structures as follows:

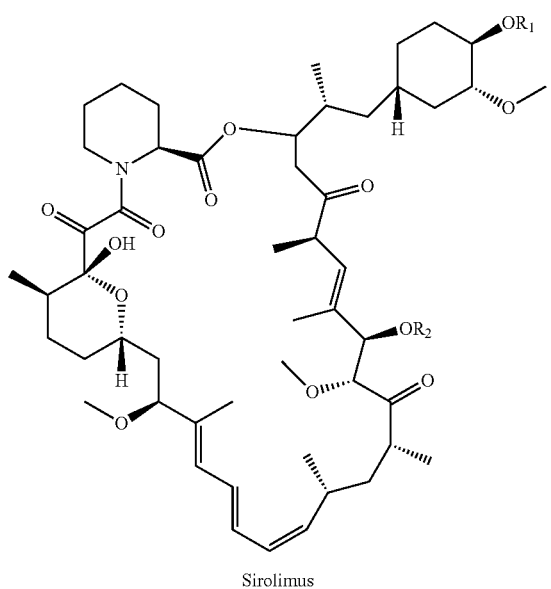

Sirolimus

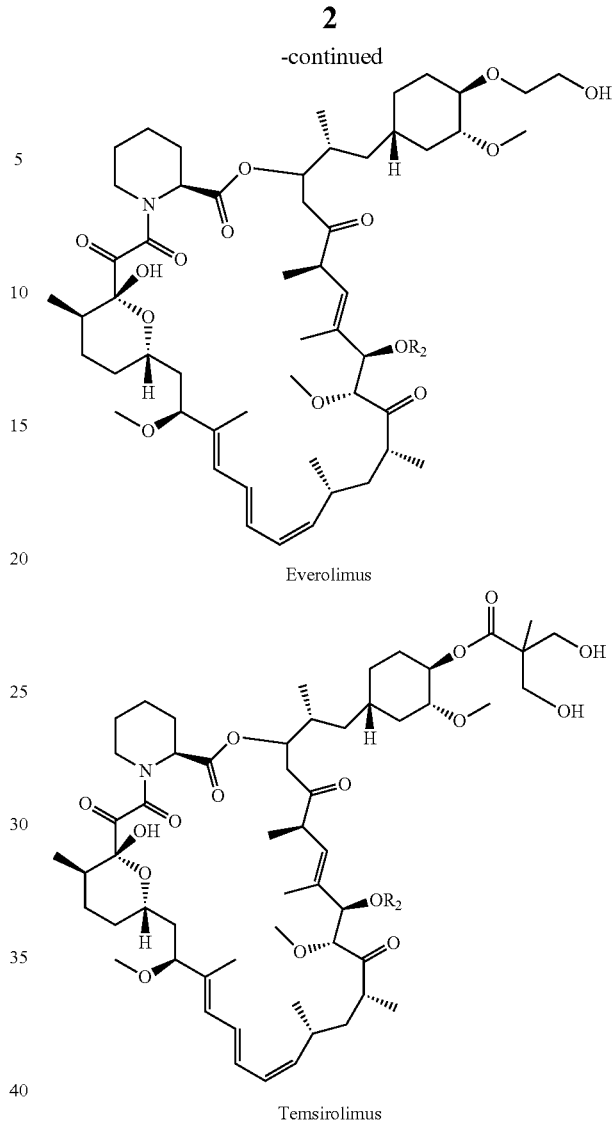

Everolimus

Temsirolimus

Rapamycin compounds were initially found to have antifungal activities, particularly a relative high inhibitory activity against *Candida albicans*.

Lately, it was found that rapamycin compounds are inhibitors for mammalian target of rapamycin (mTOR), and can act as immunodepressants. The immunosuppressive effect and the effect for preventing immune rejection after organ transplantation of the rapamycin compounds are first disclosed in the FASEB Journal (3, 3411, 1989). The action mechanism is to block the signal transduction via different cytokine receptors, so as to block the progression of G1-S phase transition of T leukomonocytes and other cells, thereby exerting an immunosuppressive effect.

Rapamycin compounds have been approved to be used in the treatment of multiple indications of tumors on clinic. For example, everolimus has been approved by FDA for the treatment of solid tumors such as advanced breast cancer, renal cell carcinoma, pancreatic cancer, angiomyolipoma and the like. Rapamycin compounds were also proved to be effective in the treatment models of diseases such as multiple sclerosis, rheumatoid arthritis, anemia and other diseases (*Can J. Physiol. Pharmcol.* 1997, 55, 48-52). And rapamycin was also reported to have a certain potential effect on prolonging the life cycle of mammals (Harrison D E, et al, *Nature*, 2009, 460, 392-395).

Rapamycin compounds can be used in multiple indications and have great application value in the clinical treatment. However, owing to the poor water-solubility as well as the poor stability in vivo, the absorption of the rapamycin compounds in vivo is low and so is the bioavailability, which is only 15%-30% (Guy Jerusalem, et al, *Breast Cancer Research and Treatment*, 2010, 125:2447-2455). And the administration of rapamycin compounds in a relatively large dosage would bring about more side effects.

In view of the above situation, enhancing the water-solubility of the rapamycin compounds can enhance their bioavailability and improve their therapeutic effect on related diseases to a great extent.

Polypeptide is an endogenous substance in human body. It consists of several amino acids and has a relatively good water solubility and an extensive bioactivity. Combination of polypeptide with a small molecule drug can enhance the solubility of the small molecule drug in one aspect, and can achieve in vivo targeted release and sustained release or improve the bioactivity with the help of the polypeptide in another aspect. For example, glutathione is a common endogenous polypeptide. It consists of glutamic acid, cysteine and glycine. Glutamic acid contains mercapto groups and has antioxidative and integrated antidotal effects. Glutathione is also a nutriment for cell growth. It can be easily taken in by cells, especially by tumor cells which propagate rapidly. A complex which prepared by the coupling of glutathione and a small molecule drug very likely has a selectivity for tumor cells which propagate rapidly and can reduce the toxicity of the anti-tumor drugs to normal cells in human body to some extent and achieve the targeted release of the small molecule drug simultaneously. In addition, glutathione is a water-soluble tripeptide. When it forms a complex with a small molecule drug, the water solubility of the small molecule drug can be improved to a great extent.

DETAILED DESCRIPTION

The present invention provides a compound of formula I or a pharmaceutically acceptable salt thereof:

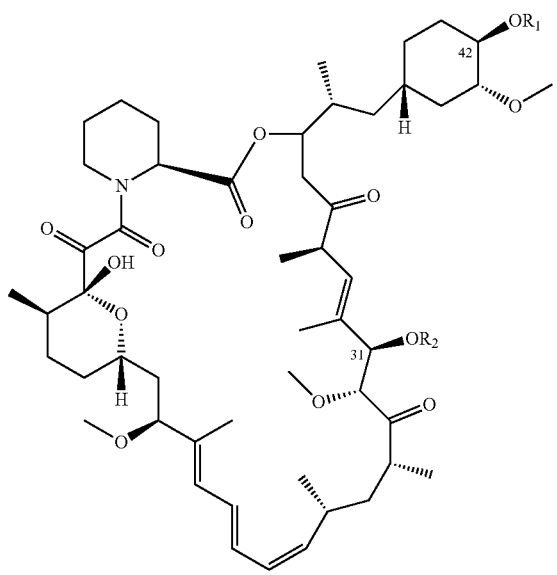

wherein,
$R_1$ is H or $R_3$;
$R_2$ is H or $R_4$—$R_5$;
but $R_1$ and $R_2$ are not simultaneously H;

$R_3$ is $R_4$—$R_5$, —$CH_2CH_2O$—$R_4$—$R_5$,

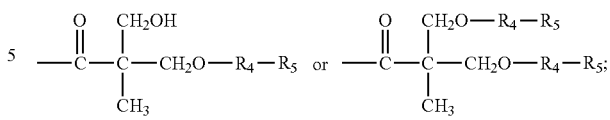

$R_4$ is

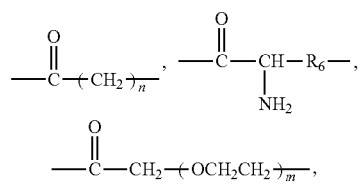

carbonyl $C_2$-$C_6$ alkenylene or carbonyl $C_2$-$C_6$ alkynylene;

n is an integer less than or equal to 6; i.e., n is 1, 2, 3, 4, 5 or 6;

m is an integer less than or equal to 6; i.e., m is 1, 2, 3, 4, 5 or 6;

$R_5$ is polypeptidyl group, preferably glutathionyl of formula II formed by dehydrogenating the mercapto group in glutathione:

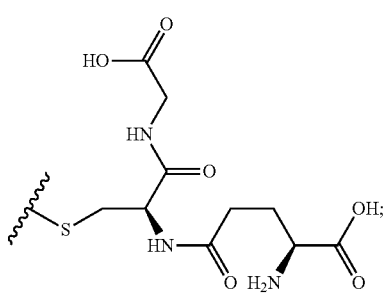

$R_6$ is $C_1$-$C_6$ alkylene, $C_2$-$C_6$ alkenylene or $C_2$-$C_6$ alkynylene.

In a preferred embodiment, $R_3$ is preferably $R_4$—$R_5$ or —$CH_2CH_2O$—$R_4$—$R_5$, wherein $R_4$ and $R_5$ are defined as those in formula I.

In a preferred embodiment, $R_4$ is preferably

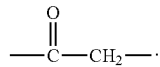

In a more preferred embodiment, $R_1$ is —$CH_2CH_2O$—$R_4$—$R_5$; further, $R_4$ is preferably

wherein n is an integer less than or equal to 6, $R_5$ is preferably glutathionyl of formula II formed by dehydrogenating the mercapto group in glutathione:

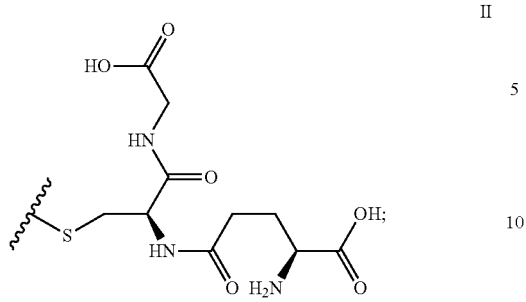
Further, $R_2$ is preferably H.
In a more preferred embodiment, the compound of formula I according to the present invention is selected from:
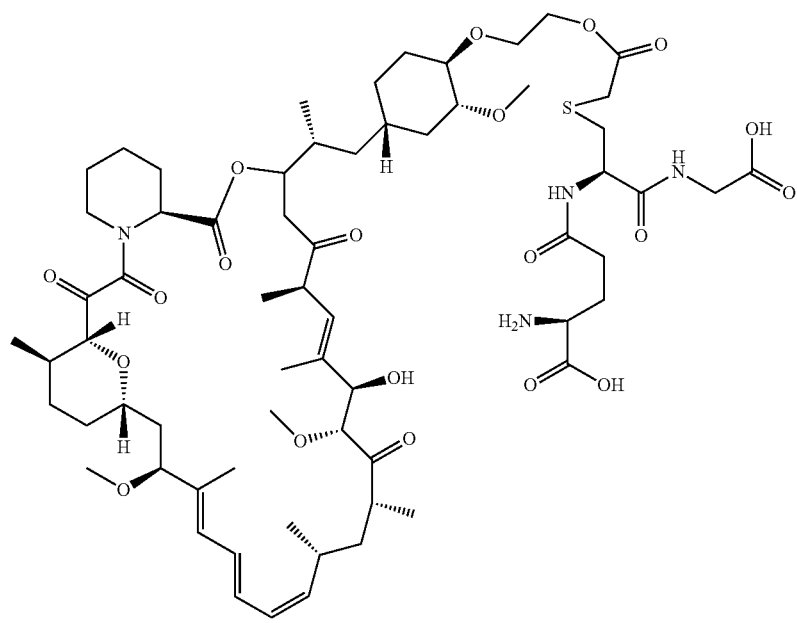
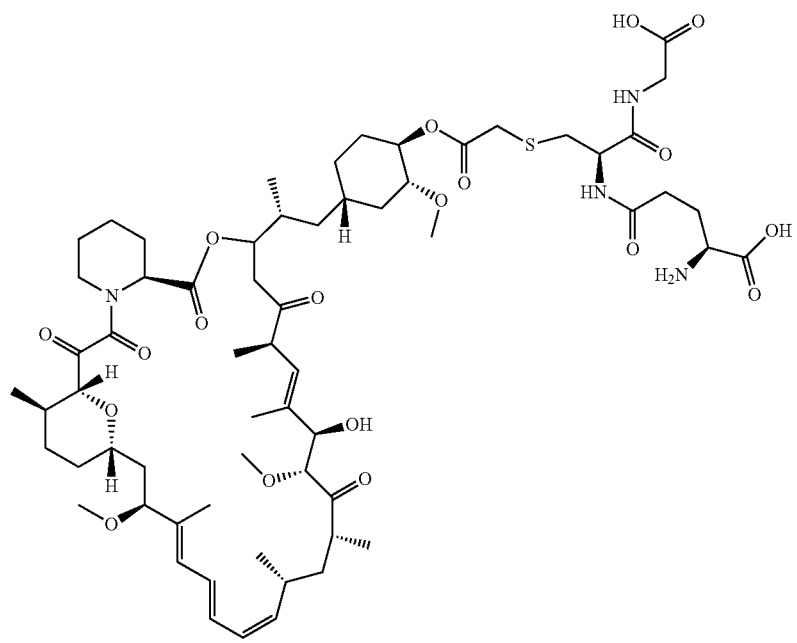

-continued
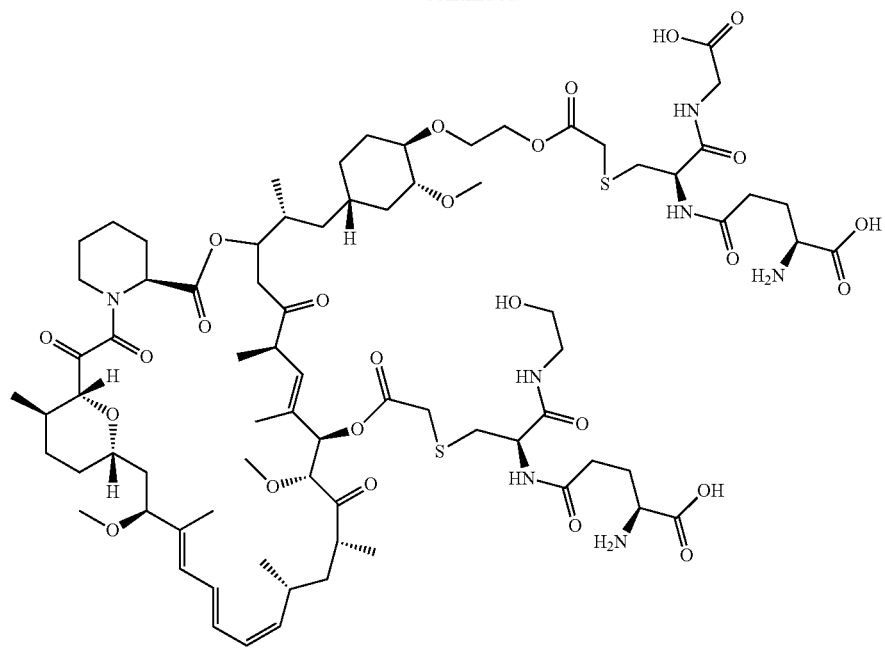
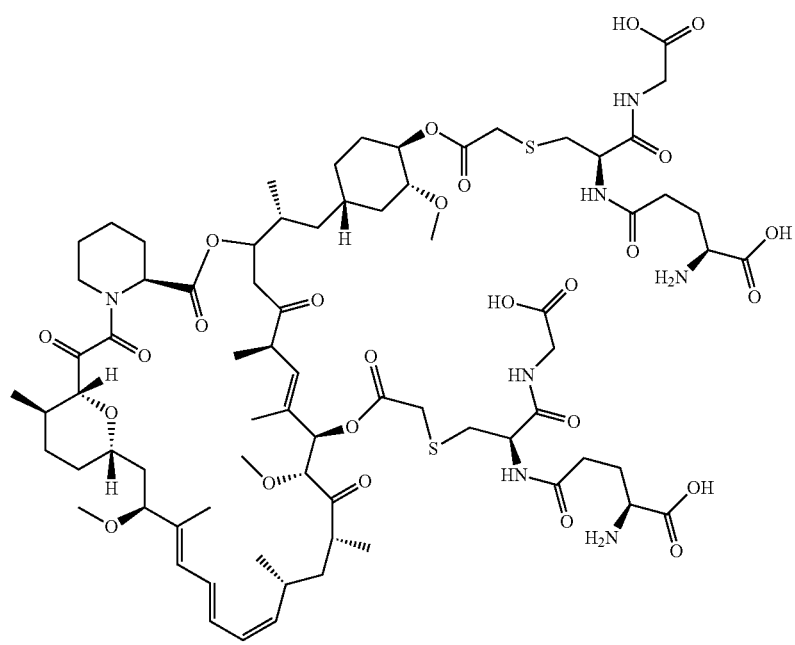

-continued
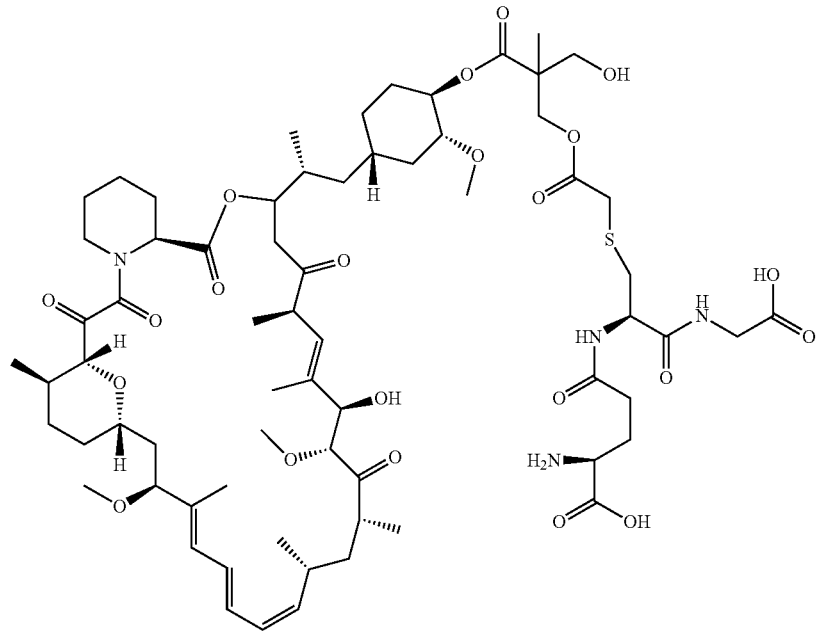
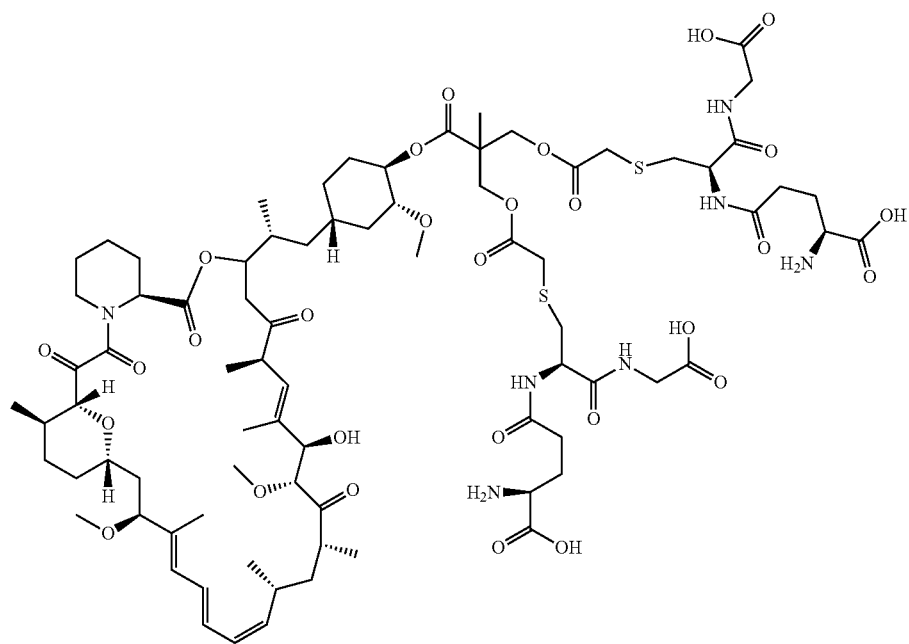

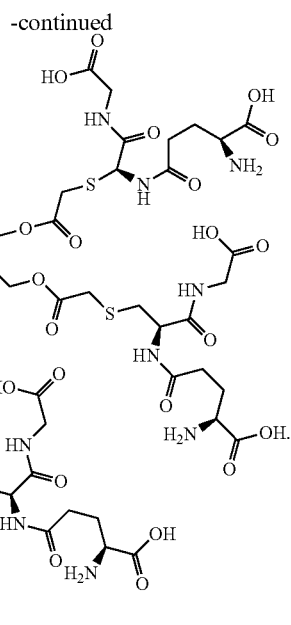

In another aspect, the present invention provides a process for preparing water-soluble rapamycin derivatives of formula I, comprising the steps of:

(a) reacting a compound of formula III with $XR_{10}COOH$ so as to obtain a compound of formula IV:

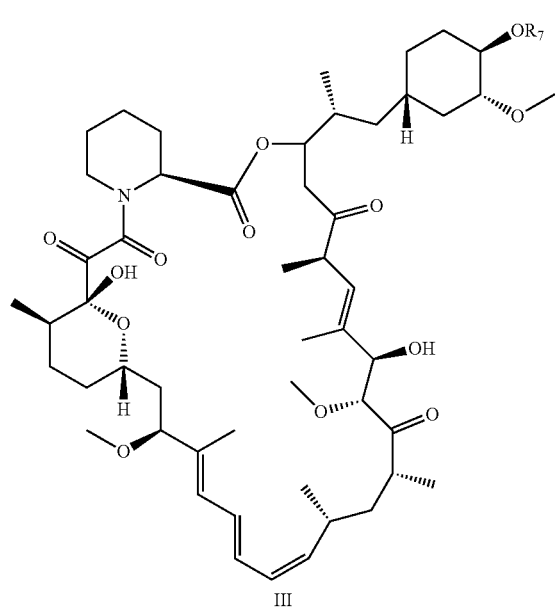

III $XR_{10}COOH \longrightarrow$

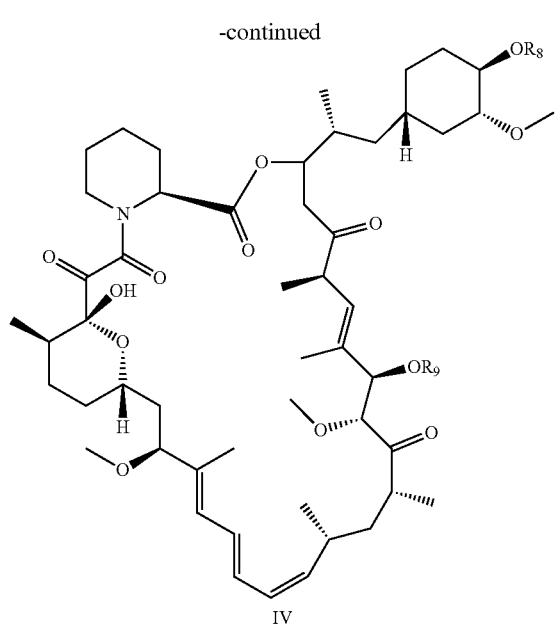

IV wherein,
$R_7$ is H, $-CH_2CH_2OH$ or

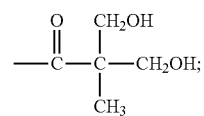

$R_8$ is H, $R_4X$, $-CH_2CH_2OR_4X$,

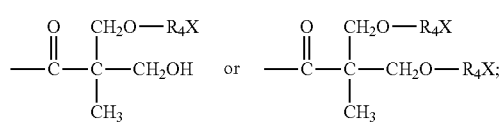

$R_9$ is H or $R_4X$;
$R_8$ and $R_9$ are not simultaneously H:

$R_{10}$ is $C_1$-$C_6$ alkylene,

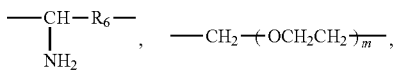

$C_2$-$C_6$ alkenylene or $C_2$-$C_6$ alkynylene;

X is a halogen atom, preferably I or Br atom;

(b) reacting the compound of formula IV obtained from step (a) with a polypeptide, so as to obtain the compound of formula I:

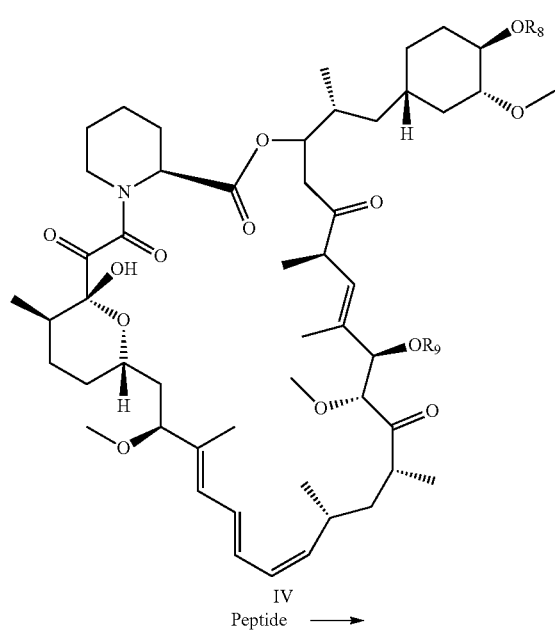

IV

Peptide ⟶

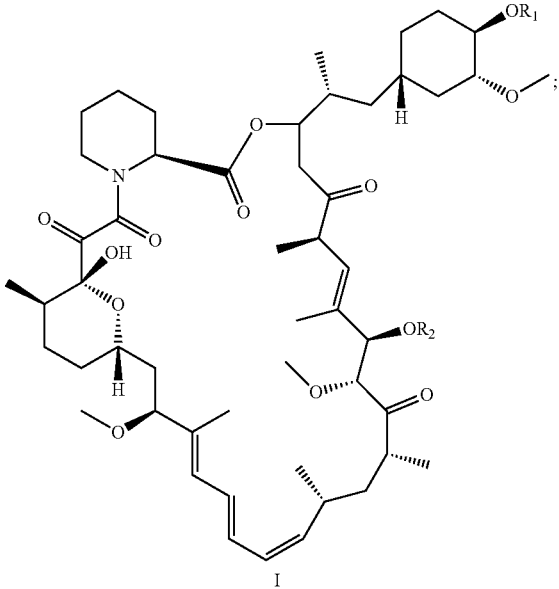

I wherein, $R_1$ is H or $R_3$;

$R_2$ is H or $R_4$—$R_5$;

but $R_1$ and $R_2$ are not simultaneously H;

$R_3$ is $R_4$—$R_5$, —$CH_2CH_2O$—$R_4$—$R_5$,

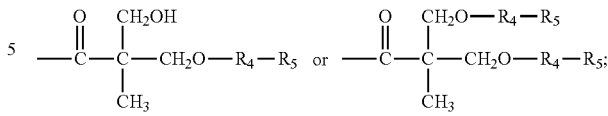

$R_4$ is independently

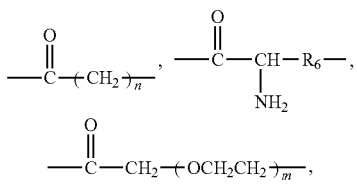

carbonyl $C_2$-$C_6$ alkenylene or carbonyl $C_2$-$C_6$ alkynylene;

n is an integer less than or equal to 6, i.e., n is 1, 2, 3, 4, 5 or 6;

m is an integer less than or equal to 6, i.e., m is 1, 2, 3, 4, 5 or 6;

$R_5$ is polypeptidyl group, preferably glutathionyl of formula II formed by dehydrogenating the mercapto group in glutathione:

II

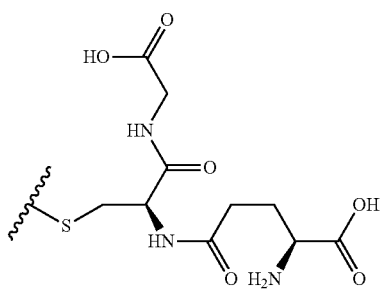

$R_6$ is $C_1$-$C_6$ alkylene, $C_2$-$C_6$ alkenylene or $C_2$-$C_6$ alkynylene.

Steps (a) and (b) is carried out with reference to the method in WO0224706 with some improvement.

Further, in step (b), the reaction of compound IV and the polypeptide is carried out in a mixed solvent which is a N,N-dimethylformamide-alcohol-water mixed solvent, wherein the alcohol is preferably ethanol.

Further, in the mixed solvent, the ratio of N,N-dimethylformamide-alcohol-water is 1:(1-5):(1:5) by volume, preferably 1:2:1 by volume.

In another aspect, the present invention provides a pharmaceutical composition comprising an effective amount of a compound of formula I or a pharmaceutically acceptable salt thereof, preferable citrate thereof; and pharmaceutical adjuvants comprising pharmaceutical carriers, excipients or combinations thereof.

The compound of formula I, the pharmaceutically acceptable salt thereof or the pharmaceutically composition thereof provided by the present invention is an immunosuppressant which can be used in the treatment or inhibition of transplant rejections. The compound of formula I according to the present invention has the suppressive effect on the growth of tumor cells and can be used in the treatment of tumors, preferably in the treatment of renal cell carcinoma, renal epithelial renal cell carcinoma, breast cancer, pancreatic cancer, lung cancer, prostate cancer, subependymal giant cell astrocytoma, or renal angiomyolipoma. The compound of formula I can also be used in the treatment of fungal infection and vascular disease.

The present invention also provides a formulation comprising a compound of formula I or a pharmaceutically acceptable salt thereof, or a pharmaceutical composition thereof. The formulation is a tablet, capsule, injection, powder, granule, drug eluting stent, pill or film.

Further, the formulation is an injection, with water for injection as vehicle.

Furthermore, the injection is a freeze-dried powder injection, with normal saline as vehicle for reconstitution.

The present invention also provides an administration method comprising administrating to a patient an effective amount of a compound of formula I or a pharmaceutically acceptable salt thereof, or a pharmaceutical composition thereof.

Further, the administration method comprises administrating to a patient by injection once weekly with an effective amount of a compound of formula I or a pharmaceutically acceptable salt thereof, or a pharmaceutical composition thereof.

The present invention provides rapamycin compounds of formula I which are modified with polypeptide, particularly rapamycin compounds modified with glutathione. The compound of formula I according to the present invention is easily soluble in normal saline and the molecular structure thereof is stable after dissolving in normal saline without an obvious degradation within 24 h. The compound of formula I according to the present invention is a prodrug of the rapamycin compounds which can gradually release the corresponding rapamycin compound in animal serum, thereby showing a sustained release effect. The compound of formula I according to the present invention exhibits better inhibitory activity against tumors as compared with the rapamycin compounds in the prior art.

Unless otherwise defined, the terms used in the invention have the meanings generally accepted in the art. Further, part of the terms used in the invention is defined as follows:

"alkyl", as a group or part of a group, indicates a linear of branched saturated aliphatic hydrocarbon groups, preferably $C_1$-$C_{10}$ alkyl, more preferably $C_1$-$C_6$ alkyl. Examples of alkyl groups include, but are not limited to, methyl, ethyl, n-propyl, isopropyl, n-butyl, isobutyl, t-butyl, sec-butyl, n-amyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylamyl, 3-methylamyl, 4-methylamyl, 2,3-dimethylbutyl and the like.

"polypeptidyl", as a group or part of a group, indicates a group formed by removal of one or more hydrogen atoms from a polypeptide or a protein, preferable a polypeptidyl formed by dehydrogenating a mercapto group comprised in a polypeptide or a protein. Examples of polypeptidyl include, but are not limited to, glutathionyl.

"A pharmaceutically acceptable salt" indicates certain salts of the compounds described above which can maintain their original bioactivities and are suitable for pharmaceutical applications. A pharmaceutically acceptable salt of a compound of formula I can be a salt formed by reacting said compound with a suitable acid including inorganic and organic acids, such as acetic acid, benzene sulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, malic acid, maleic acid, mandelic acid, methanesulfonic acid, nitric acid, phosphoric acid, succinic acid, sulfuric acid, tartaric acid, p-toluenesulfonic acid and the like.

DRAWINGS

EXAMPLES

Figure 1:
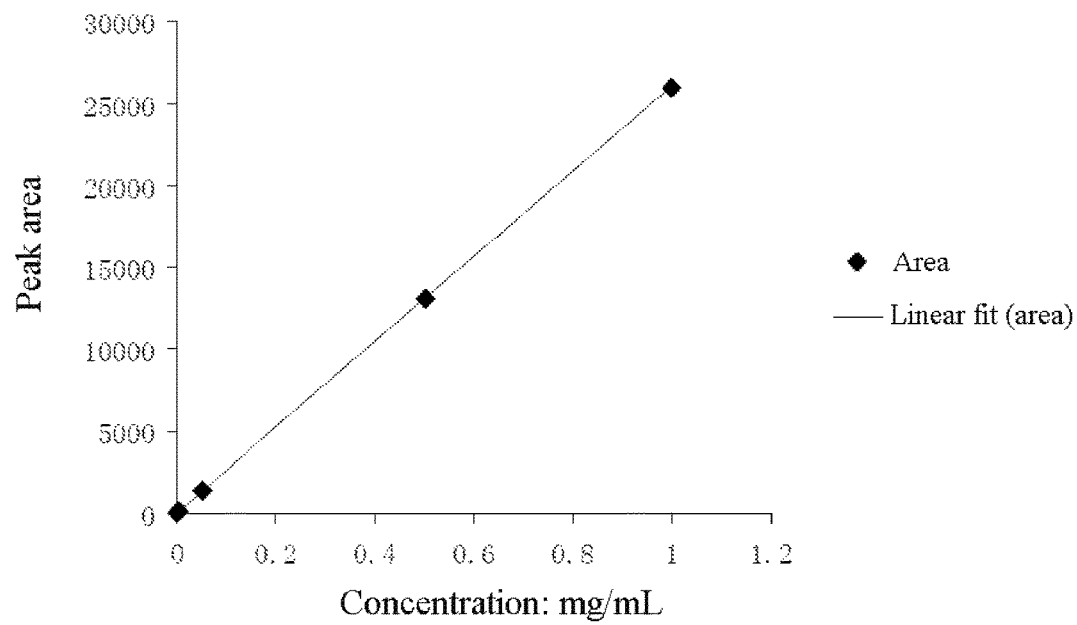
FIG. 1 is a standard curve of peak area versus concentration of everolimus obtained from example 11, with peak area as the vertical coordinate and concentration with a unit of mg/mL as the horizontal coordinate.

The present invention will be more specifically understood by the person skilled in the art from the following examples which, however, should not be understood to limit the invention in any way.

In the following examples, unless otherwise indicated, all the temperatures refer to centigrade degree; all the starting materials and agents are commercially available; in addition, the starting materials and agents which are commercially available are used without further purification.

The preparative liquid chromatography (preparative HPLC) mentioned in the following examples is carried out under the following conditions:

Chromatographic column: Kromasil-$C_{18}$ column, 10 μm, 100DAC preparative column; mobile phase: 47% acetonitrile-100 mmol/L ammonium acetate aqueous solution, isocratic elution for 40 min; detection wavelength: 254 nm; column temperature: 25° C.; flow rate: 200 ml/min.

The detection liquid chromatography (preparative HPLC) mentioned in the following examples is carried out under the following conditions:

Chromatographic column: Xselect CSH-$C_{18}$ column, (4.6 mm×250 mm, 5 μm); mobile phase A: 0.1% trifluoroacetic acid aqueous solution, B:acetonitrile, gradient elution (0→10 min, A:B=75:25, 10→15 min, A:B=75:25→65:35, 15→20 min, A:B=5:95, 20→30 min, A:B=5:95); detection wavelength: 280 nm; column temperature: 30° C.; flow rate: 1 ml/min, injection volume: 10 μl.

The following examples are merely used to illustrate the preparation method for specific compounds according to the present invention, but do not intend to limit the preparation method according to the present invention in any way. Compounds which are not listed in the following preparation examples can also be prepared by a synthetic route and method similar with those conducted in the following examples, with difference merely in that the starting materials may be adaptively selected and the reaction conditions may be slightly adaptively adjusted according to common knowledge when necessary.

Representative examples of the preparation process and related study examples of the present invention are described as follows:

Example 1

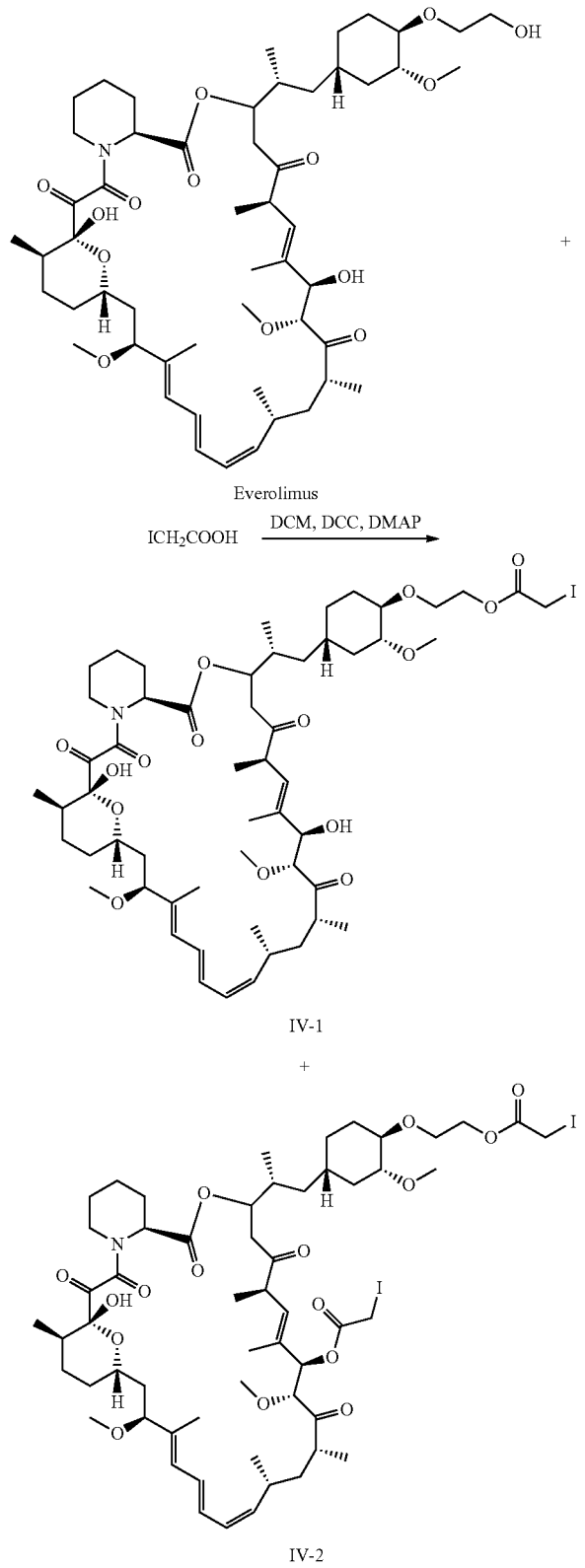

To a 100 mL three-neck flask, everolimus (5.0 g, 5.2 mmol) and iodoacetic acid (1.94 g, 10.4 mmol) were added, followed by addition of 20 mL dichloromethane (DCM). The mixture was stirred till all the solid dissolved. Then, the mixture was cooled to 0-5° C. and dicyclohexyl carbodiimide (DCC, 2.36 g, 11.4 mmol) was added, which was stirred at 0-5° C. for 10-15 min. To the reaction mixture, 4-dimethylamino pyridine (DMAP, 0.63 g, 5.2 mmol) was added. The reacted mixture was warmed to room temperature and stirred for 16-24 h. After the reaction completion (monitored by TLC), and the insoluble solid was filtrated via using a Büchner funnel. Then, the filtrate was concentrated to dry under reduced pressure at 30-40° C. The obtained slurry was purified by silica gel column (eluted with n-hexane/ethyl acetate=5:1-2:1) to give everolimus monohaloacetate IV-1 (2.15 g, 1.9 mmol) and everolimus dihaloacetate W-2 (2.60 g, 2.0 mmol), respectively.

Everolimus Monohaloacetate IV-1:

$^1$H NMR (400 MHz, CDCl$_3$) δ 6.35 (dt, J=24.8, 14.8 Hz, 1H), 6.19-6.09 (m, 1H), 5.93 (dd, J=30.1, 10.5 Hz, 1H), 5.60-5.45 (m, 1H), 5.41 (d, J=9.9 Hz, 1H), 5.27 (t, J=7.2 Hz, 1H), 5.15 (dt, J=11.6, 5.5 Hz, 1H), 4.34-4.24 (m, 2H), 4.16 (ddd, J=21.4, 14.1, 6.6 Hz, 2H), 3.91-3.75 (m, 2H), 3.73 (d, J=7.1 Hz, 2H), 3.67 (dd, J=14.5, 6.8 Hz, 1H), 3.57 (d, J=13.5 Hz, 1H), 3.44 (d, J=10.3 Hz, 4H), 3.40-3.28 (m, 4H), 3.21-3.00 (m, 5H), 2.84 (dd, J=17.7, 7.0 Hz, 1H), 2.72 (dd, J=16.4, 5.5 Hz, 2H), 2.58 (dd, J=16.7, 6.4 Hz, 1H), 2.33 (d, J=12.9 Hz, 1H), 2.10-1.89 (m, 6H), 1.75 (s, 6H), 1.71-1.57 (m, 8H), 1.54-1.40 (m, 4H), 1.38-1.19 (m, 8H), 1.12 (dd, J=19.6, 6.8 Hz, 4H), 1.05 (d, J=6.3 Hz, 4H), 0.99 (d, J=6.4 Hz, 2H), 0.95 (d, J=6.5 Hz, 2H), 0.93-0.82 (m, 4H), 0.71 (dt, J=16.5, 8.3 Hz, 1H). ESI-MS: [M+Na]$^+$1149.58, C$_{55}$H$_{84}$INO$_{15}$.

Everolimus Dihaloacetate IV-2:

$^1$H NMR (400 MHz, CDCl$_3$) δ 6.34 (dt, J=24.7, 14.8 Hz, 1H), 6.18-6.11 (m, 1H), 5.93 (dd, J=29.8, 10.2 Hz, 1H), 5.62-5.48 (m, 1H), 5.40 (d, J=9.9 Hz, 1H), 5.28 (t, J=7.0 Hz, 1H), 5.15 (dt, J=12.0, 5.6 Hz, 1H), 4.34-4.20 (m, 2H), 4.16 (ddd, J=21.3, 12.6, 6.5 Hz, 2H), 3.90-3.78 (m, 2H), 3.75 (d, J=7.5 Hz, 2H), 3.70 (d, J=13.5 Hz, 1H), 3.67 (dd, J=14.8, 6.3 Hz, 1H), 3.44 (d, J=10.0 Hz, 4H), 3.40-3.30 (m, 4H), 3.21-2.98 (m, 5H), 2.82 (dd, J=17.8, 7.2 Hz, 1H), 2.70 (dd, J=16.5, 5.8 Hz, 2H), 2.60 (dd, J=16.8, 6.6 Hz, 1H), 2.33 (d, J=12.8 Hz, 1H), 2.12-1.91 (m, 6H), 1.73 (s, 6H), 1.70-1.58 (m, 8H), 1.55-1.43 (m, 4H), 1.37-1.21 (m, 8H), 1.12 (dd, J=19.8, 6.8 Hz, 4H), 1.08 (d, J=6.5 Hz, 4H), 0.98 (d, J=6.5 Hz, 2H), 0.93 (d, J=6.5 Hz, 2H), 0.92-0.80 (m, 6H), 0.75 (dt, J=14.8, 8.0 Hz, 1H). ESI-MS: [M+Na]$^+$1317.41, C$_{57}$H$_{85}$I$_2$NO$_{16}$.

Example 2

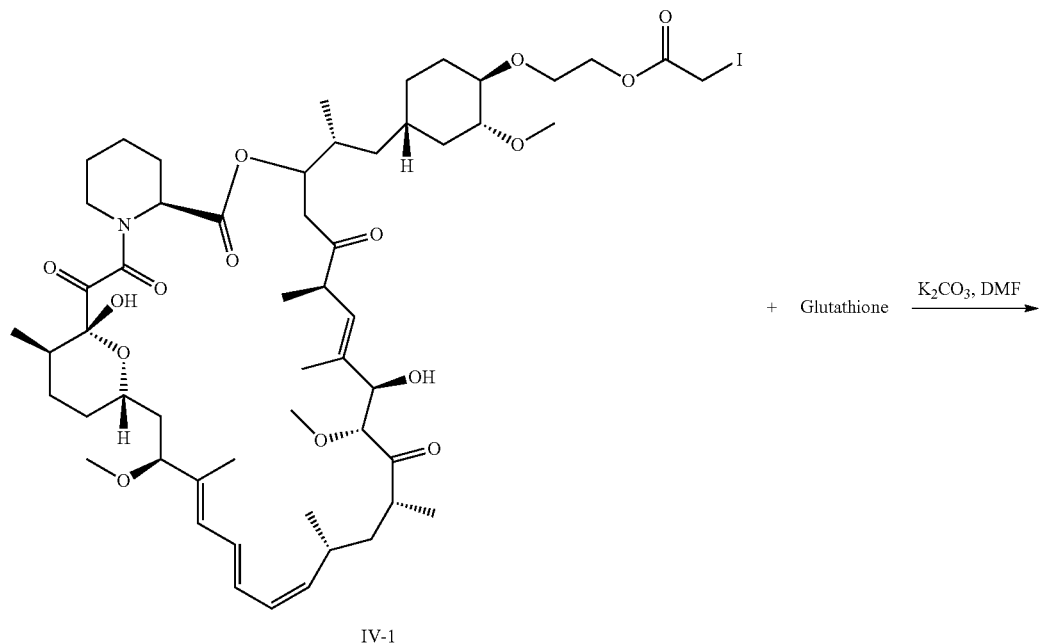

IV-1

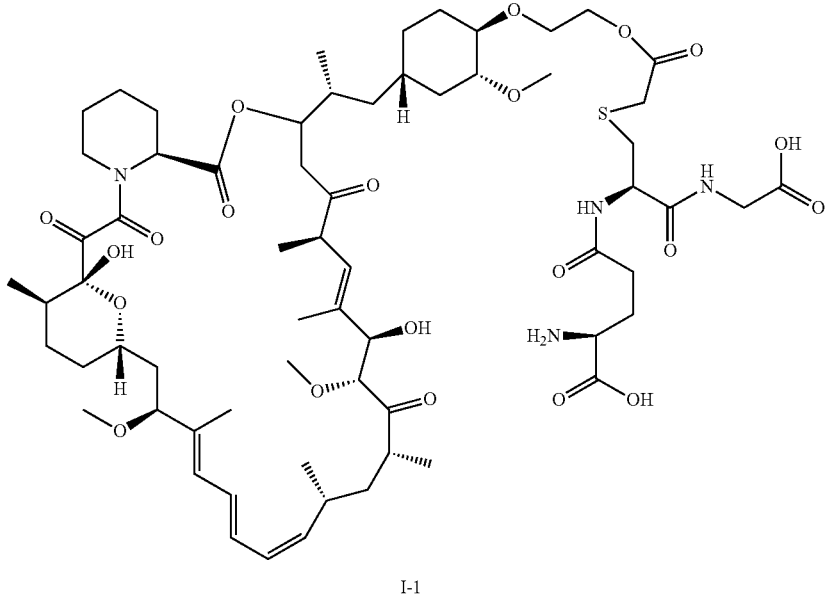

I-1

To a 100 mL three-neck flask, everolimus monohaloacetate IV-1 (1 g, 0.9 mmol) and glutathione (0.55 g, 1.8 mmol) were added, followed by addition of 5 mL N,N-dimethylformamide (DMF). The mixture was stirred till the solid suspended in the N,N-dimethylformamide. $K_2CO_3$ (124.2 mg, 0.9 mmol) was added to the suspension, to which 5 mL $H_2O$ and 10 mL ethanol were then added. After vigorous stirred for 10 min, the reaction mixture turned clear. The reaction mixture was stirred over night at r.t. Reaction completion of compound IV-1 was monitored by HPLC, and the reaction mixture was concentrated to dry under reduced pressure at 45-55° C. The obtained slurry was purified by preparative HPLC to obtain compound I-1 (0.98 g, 0.75 mmol).

Compound I-1: $^1$H NMR (400 MHz, $CD_3OD+CDCl_3$) δ 6.49-6.39 (m, 1H), 6.19 (ddd, J=30.9, 22.1, 11.0 Hz, 3H), 5.55-5.39 (m, 1H), 5.26 (d, J=10.0 Hz, 1H), 5.10 (s, 2H), 4.64 (s, 1H), 4.24 (d, J=24.1 Hz, 3H), 4.08 (d, J=27.6 Hz, 2H), 3.83 (s, 4H), 3.73-3.51 (m, 3H), 3.50-3.24 (m, 12H), 3.12 (d, J=26.5 Hz, 7H), 2.93 (s, 1H), 2.79 (d, J=17.6 Hz, 1H), 2.50 (dd, J=27.1, 18.3 Hz, 4H), 2.25 (d, J=13.3 Hz, 2H), 2.15 (s, 2H), 2.05 (s, 4H), 1.93-1.53 (m, 16H), 1.43 (dd, J=27.1, 14.5 Hz, 5H), 1.29 (s, 2H), 1.25-1.11 (m, 4H), 1.06 (d, J=4.6 Hz, 4H), 1.02-0.79 (m, 13H), 0.76 (d, J=11.9 Hz, 2H)0 HR-ESI-MS: $[M+H]^+$ 1305.6671, $C_{65}H_{100}N_4O_{21}S$.

Example 3

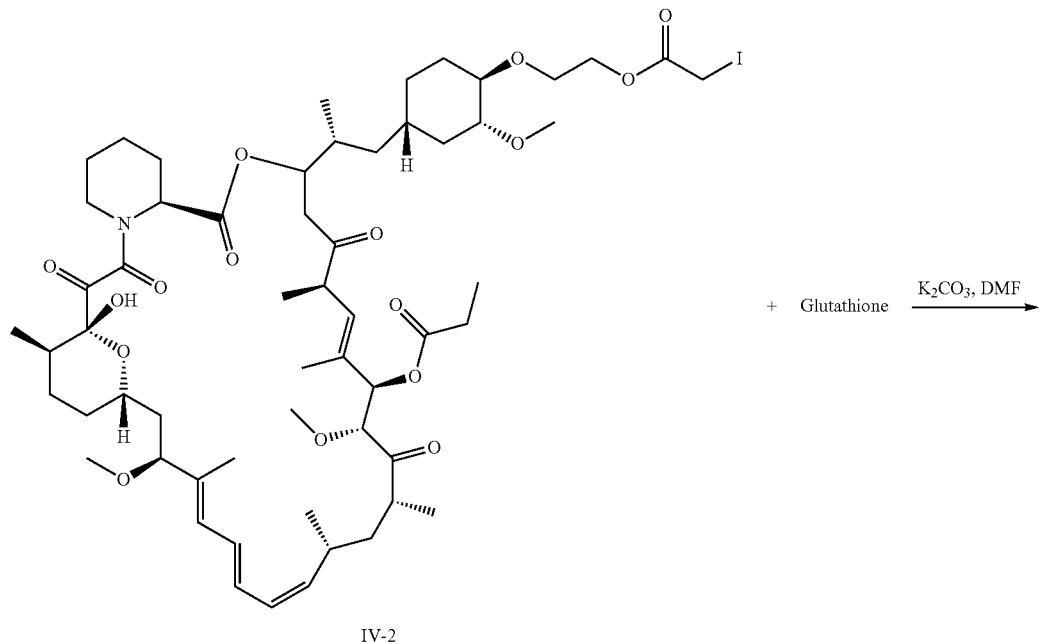

IV-2

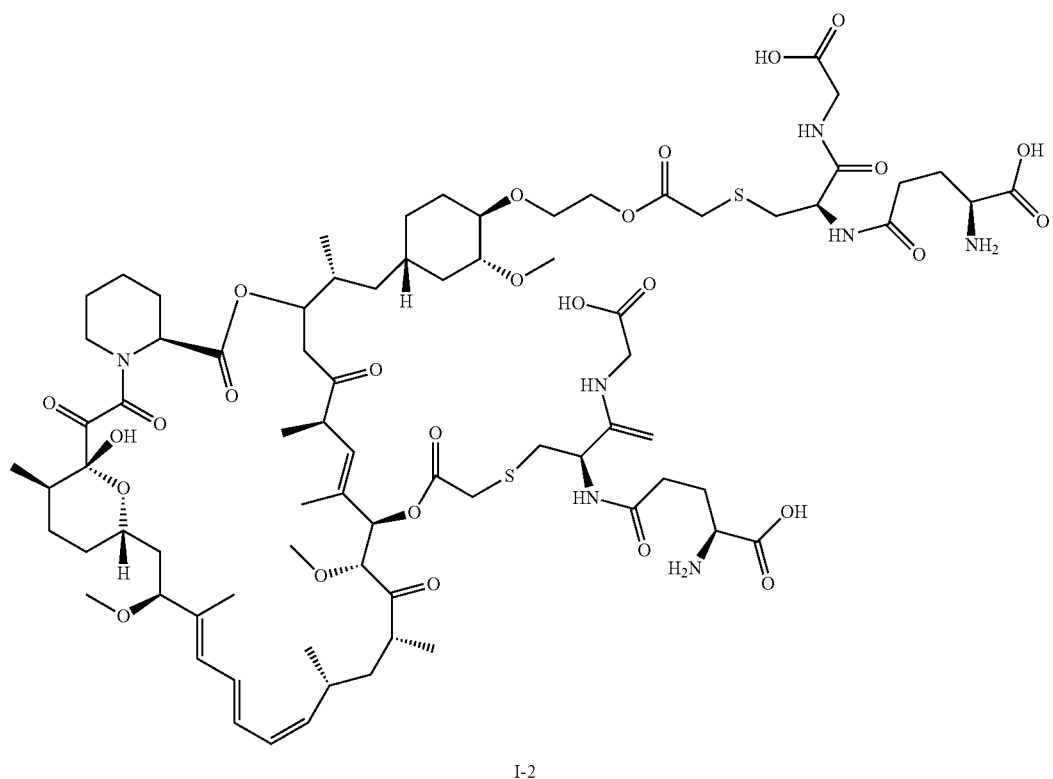

I-2

To a 250 mL three-neck flask everolimus dihaloacetate IV-2 (1.5 g, 1.2 mmol) and glutathione (1.17 g, 3.6 mmol) were added, followed by addition of 10 mL N,N-dimethylformamide. The mixture was stirred till the solid suspended in the N,N-dimethylformamide. $K_2CO_3$ (248.4 mg, 1.8 mmol) was added to the suspension, to which 10 mL $H_2O$ and 20 mL ethanol were then added. After vigorous stirred for 15 min, the reaction mixture turned clear. The reaction mixture was stirred over night at r.t. Reaction completion of compound IV-2 was monitored by HPLC, and the reaction mixture was concentrated to dry under reduced pressure at 45-55° C. The obtained slurry was purified by preparative HPLC to obtain compound I-2 (0.51 g, 0.31 mmol).

Compound I-2: $^1$H NMR (400 MHz, CD$_3$OD+CDCl$_3$) δ 6.48-6.37 (m, 1H), 6.19 (ddd, J=29.8, 21.5, 10.0 Hz, 3H), 5.54-5.40 (m, 1H), 5.26 (d, J=10.1 Hz, 1H), 5.11 (s, 2H), 4.62 (s, 1H), 4.24 (d, J=23.5 Hz, 3H), 4.10 (d, J=27.6 Hz, 2H), 3.85 (s, 4H), 3.74-3.55 (m, 3H), 3.52-3.20 (m, 16H), 3.10 (d, J=25.7 Hz, 7H), 2.92 (s, 1H), 2.81 (d, J=17.6 Hz, 1H), 2.48 (dd, J=28.0, 17.8 Hz, 4H), 2.30 (d, J=13.5 Hz, 2H), 2.17 (s, 2H), 2.04 (s, 4H), 1.97-1.48 (m, 21H), 1.43 (dd, J=26.8, 14.2 Hz, 5H), 1.30 (s, 2H), 1.27-1.10 (m, 4H), 1.05 (d, J=4.6 Hz, 4H), 1.01-0.74 (m, 17H), 0.71 (d, J=12.0 Hz, 2H). HR-ESI-MS: [M+H]$^+$ 1640.5401, C$_{77}$H$_{117}$N$_7$O$_{28}$S$_2$.

Example 4

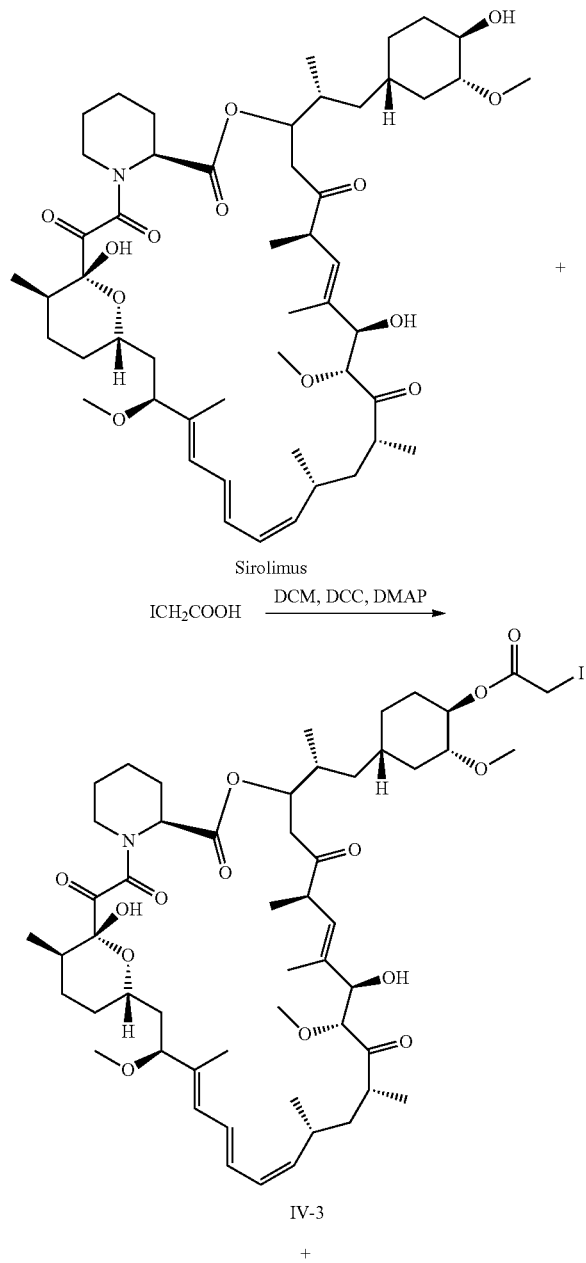

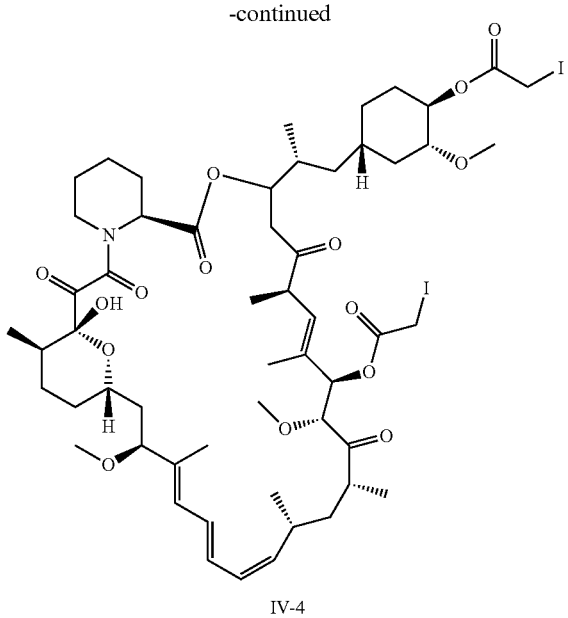

To a 100 mL three-neck flask, sirolimus (4.0 g, 4.4 mmol) and iodoacetic acid (1.64 g, 8.8 mmol) were added, followed by addition of 20 mL dichloromethane. The mixture was stirred till all the solid dissolved. The mixed mixture was cooled to 0-5° C. and dicyclohexyl carbodiimide (2.0 g, 11.4 mmol) was added. The mixture was stirred at 0-5° C. for 10-15 min. To the reaction mixture 4-dimethylamino pyridine (0.54 g, 4.4 mmol) was added. The reacted mixture was warmed to room temperature and stirred for 16-24 h. Reaction completion of sirolimus was monitored by TLC, and the insoluble solid was filtrated via a Büchner funnel. The filtrate was concentrated to dry under reduced pressure at 30-40° C. The obtained slurry was purified by silica gel column (eluted with n-hexane/ethyl acetate=10:1-2:1) to give sirolimus monohaloacetate IV-3 (1.8 g, 1.7 mmol) and sirolimus dihaloacetate IV-4 (1.0 g, 0.8 mmol), respectively.

Sirolimus Monohaloacetate IV-3:
$^1$H NMR (400 MHz, CDCl$_3$) δ 6.34 (dt, J=24.8, 14.8 Hz, 1H), 6.15-6.09 (m, 1H), 5.95 (dd, J=30.0, 10.2 Hz, 1H), 5.58-5.46 (m, 1H), 5.40 (d, J=9.9 Hz, 1H), 5.28 (t, J=7.2 Hz, 1H), 5.14 (dt, J=11.6, 5.5 Hz, 1H), 4.33-4.28 (m, 2H), 4.18 (ddd, J=21.4, 14.1, 6.6 Hz, 2H), 3.68 (dd, J=14.5, 6.8 Hz, 1H), 3.56 (d, J=13.5 Hz, 1H), 3.44 (d, J=10.3 Hz, 4H), 3.40-3.26 (m, 4H), 3.20-3.00 (m, 5H), 2.85 (dd, J=17.7, 7.0 Hz, 1H), 2.70 (dd, J=16.4, 5.5 Hz, 2H), 2.57 (dd, J=16.7, 6.4 Hz, 1H), 2.30 (d, J=12.9 Hz, 1H), 2.12-1.90 (m, 6H), 1.75 (s, 6H), 1.71-1.58 (m, 8H), 1.55-1.42 (m, 4H), 1.38-1.20 (m, 8H), 1.15 (dd, J=19.6, 6.8 Hz, 4H), 1.05 (d, J=6.3 Hz, 4H), 0.98 (d, J=6.4 Hz, 2H), 0.95 (d, J=6.5 Hz, 2H), 0.95-0.85 (m, 4H), 0.70 (dt, J=16.5, 8.3 Hz, 1H). ESI-MS:[M+H]$^+$ 1083.46, C$_{53}$H$_{80}$INO$_{14}$.

Sirolimus Dihaloacetate IV-4:
$^1$H NMR (400 MHz, CDCl$_3$) δ 6.33 (dt, J=24.7, 14.6 Hz, 1H), 6.16-6.11 (m, 1H), 5.98 (dd, J=25.2, 12.0 Hz, 1H), 5.62-5.49 (m, 1H), 5.38 (d, J=9.8 Hz, 1H), 5.26 (t, J=7.0 Hz, 1H), 5.12 (dt, J=12.0, 5.5 Hz, 1H), 4.30-4.21 (m, 2H), 4.15 (ddd, J=20.7, 14.0, 6.5 Hz, 2H), 3.72 (d, J=13.5 Hz, 1H), 3.68 (dd, J=14.2, 7.2 Hz, 1H), 3.45 (d, J=10.3 Hz, 4H), 3.39-3.32 (m, 4H), 3.21-2.99 (m, 5H), 2.83 (dd, J=18.7, 7.2 Hz, 1H), 2.74 (dd, J=16.5, 5.6 Hz, 2H), 2.62 (dd, J=16.8, 6.5 Hz, 1H), 2.35 (d, J=12.6 Hz, 1H), 2.10-1.95 (m, 6H), 1.77 (s, 6H), 1.70-1.62 (m, 8H), 1.52-1.45 (m, 4H), 1.38-1.23 (m, 8H), 1.15 (dd, J=19.6, 6.8 Hz, 4H), 1.10 (d, J=6.2 Hz, 4H), 0.97 (d, J=6.3 Hz, 2H), 0.95 (d, J=6.5 Hz, 2H), 0.92-0.82 (m, 6H), 0.73 (dt, J=16.5, 8.4 Hz, 1H). ESI-MS: [M+H]$^+$ 1251.04, $C_{55}H_{81}I_2NO_{15}$.

Example 5

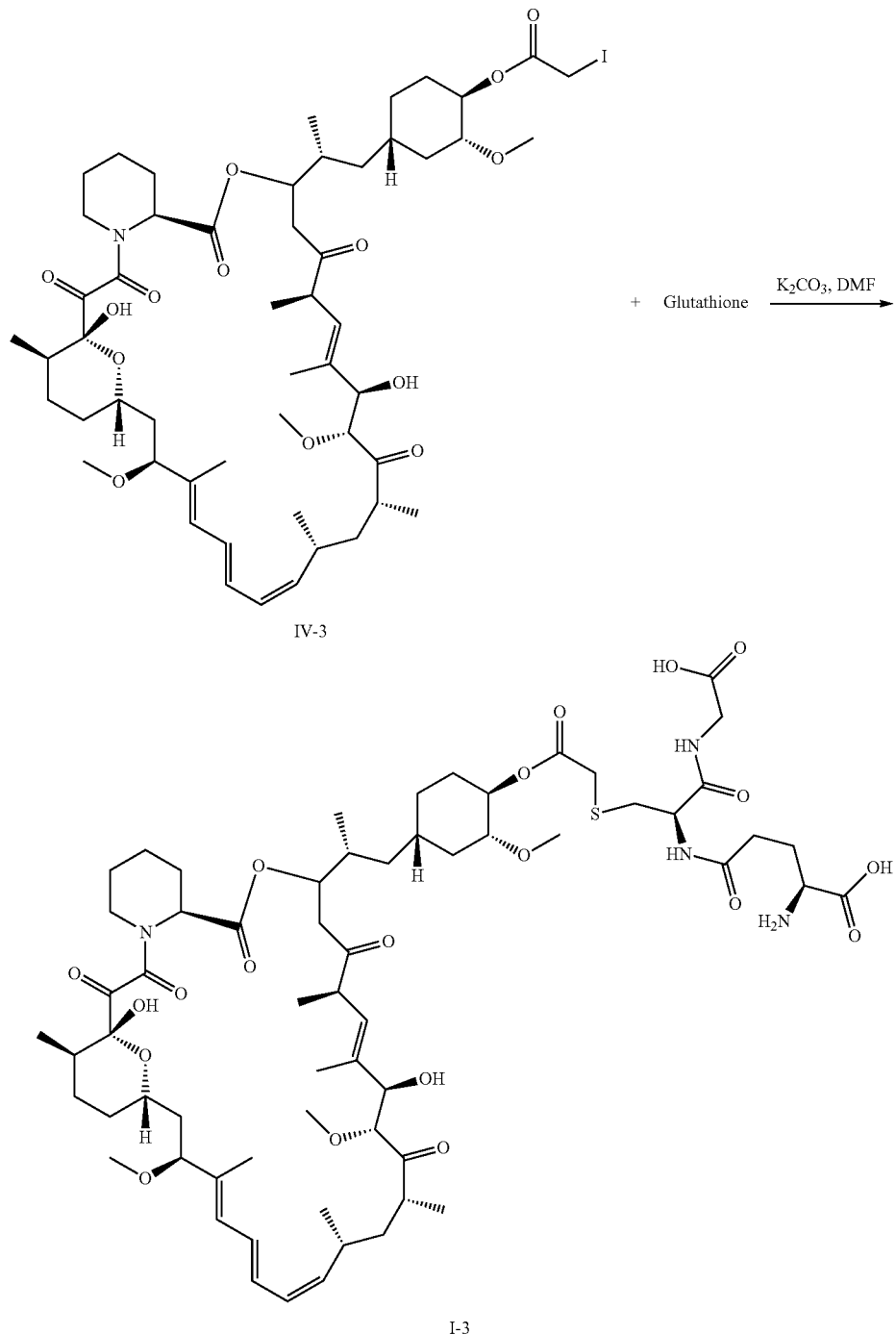

IV-3

+ Glutathione $\xrightarrow{K_2CO_3, DMF}$

I-3

To a 100 mL three-neck flask, sirolimus monohaloacetate IV-3 (1.2 g, 1.1 mmol) and glutathione (0.68 g, 2.2 mmol) were added, followed by addition of 6 mL N,N-dimethylformamide. The mixture was stirred till the solid suspended in the N,N-dimethylformamide. $K_2CO_3$ (151.8 mg, 1.1 mmol) was added to the suspension, to which 6 mL $H_2O$ and 12 mL ethanol were then added. After vigorously stirred for 15 min, the reaction mixture turned clear. The reaction mixture was stirred over night at r.t. Reaction completion of compound IV-3 was monitored by HPLC, and the reaction mixture was concentrated to dry under reduced pressure at 45-55° C. The obtained slurry was purified by preparative HPLC to give compound I-3 (0.83 g, 0.75 mmol).

Compound I-3: $^1$H NMR (400 MHz, CD$_3$OD+CDCl$_3$) δ 6.48-6.40 (m, 1H), 6.18 (ddd, J=25.8, 20.5, 10.8 Hz, 3H), 5.56-5.41 (m, 1H), 5.28 (d, J=12.0 Hz, 1H), 5.17 (s, 2H), 4.65 (s, 1H), 4.20 (d, J=22.5 Hz, 3H), 4.07 (d, J=26.0 Hz, 2H), 3.80 (s, 4H), 3.73-3.53 (m, 3H), 3.45-3.22 (m, 12H), 3.13 (d, J=25.5 Hz, 7H), 2.95 (s, 1H), 2.84 (d, J=17.8 Hz, 1H), 2.55 (dd, J=26.0, 18.2 Hz, 4H), 2.26 (d, J=13.5 Hz, 2H), 2.15 (s, 2H), 2.01 (s, 4H), 1.93-1.55 (m, 14H), 1.47 (dd, J=27.3, 15.5 Hz, 5H), 1.38 (s, 2H), 1.25-1.13 (m, 4H), 1.07 (d, J=4.7 Hz, 4H), 1.03-0.78 (m, 12H), 0.76 (d, J=11.8 Hz, 2H). ESI-MS: [M+H]$^+$ 1261.52, $C_{63}H_{96}N_4O_{20}S$.
Example 6
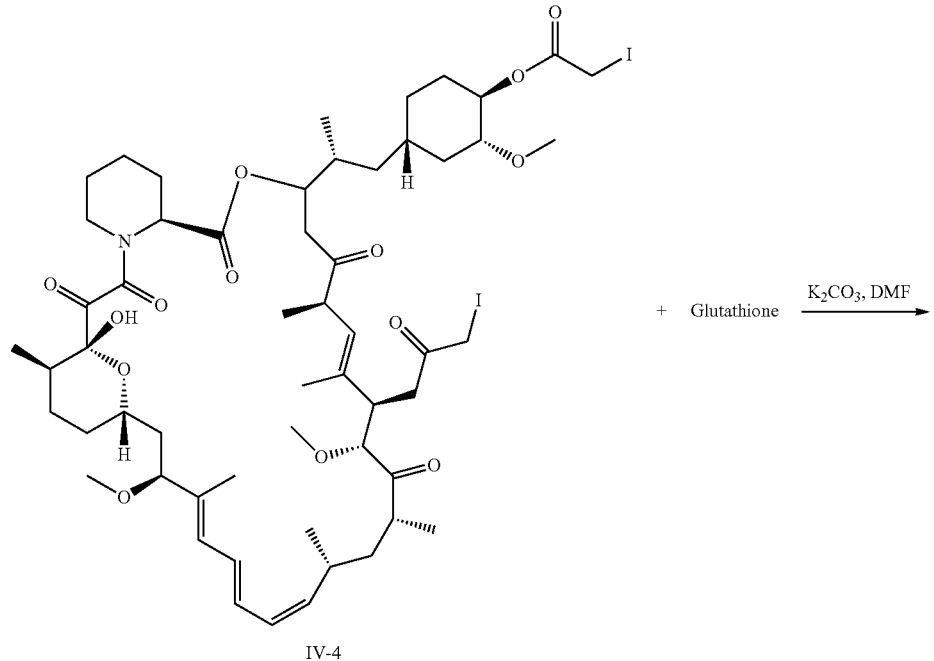
IV-4
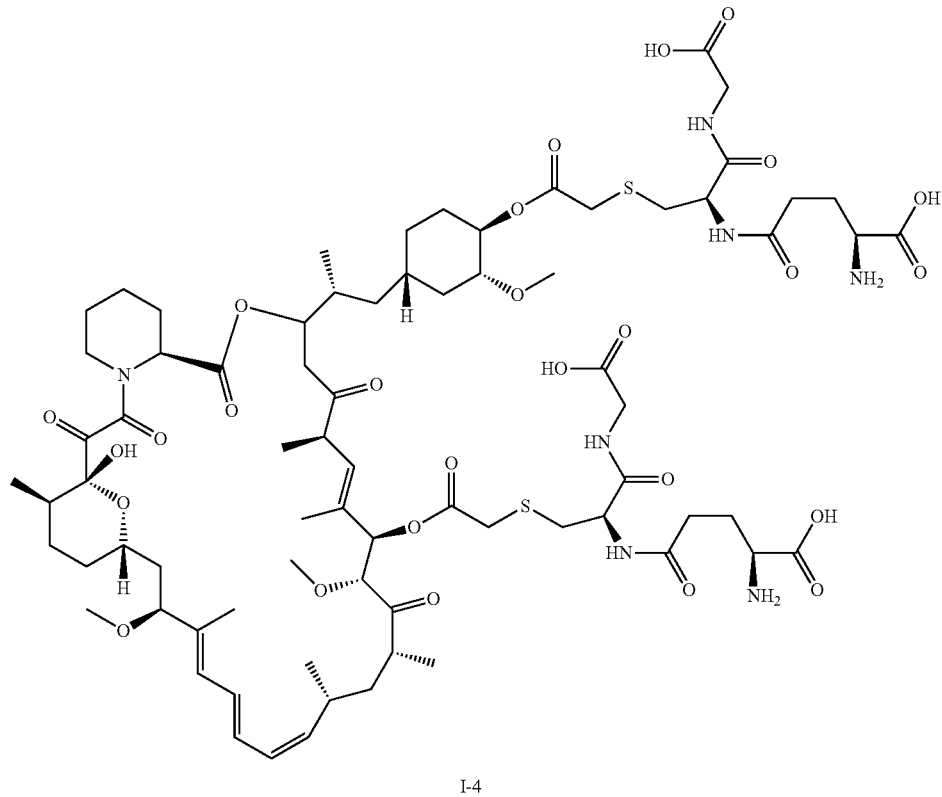
I-4

To a 250 mL three-neck flask, sirolimus dihaloacetate IV-4 (0.8 g, 0.64 mmol) and glutathione (0.59 g, 1.92 mmol) were added, followed by addition of 5 mL N,N-dimethylformamide. The mixture was stirred till the solid suspended in the N,N-dimethylformamide. $K_2CO_3$ (132.5 mg, 0.96 mmol) was added to the suspension, to which 5 mL $H_2O$ and 10 mL ethanol were then added. After vigorously stirred for 15 min, the reaction mixture turned clear. The reaction mixture was stirred over night at r.t. Reaction completion of compound IV-4 was monitored by HPLC. The reaction mixture was concentrated to dry under reduced pressure at 45-55° C. The obtained slurry was purified by preparative HPLC to give compound I-4 (0.35 g, 0.22 mmol).

Compound I-4: $^1$H NMR (400 MHz, $CD_3OD+CDCl_3$) δ 6.46-6.38 (m, 1H), 6.16 (ddd, J=29.8, 20.1, 11.5 Hz, 3H), 5.55-5.42 (m, 1H), 5.25 (d, J=10.2 Hz, 1H), 5.12 (s, 2H), 4.63 (s, 1H), 4.23 (d, J=24.5 Hz, 3H), 4.03 (d, J=28.2 Hz, 2H), 3.83 (s, 4H), 3.75-3.58 (m, 3H), 3.52-3.26 (m, 14H), 3.16 (d, J=25.6 Hz, 7H), 2.92 (s, 1H), 2.78 (d, J=17.8 Hz, 1H), 2.51 (dd, J=27.1, 18.2 Hz, 4H), 2.23 (d, J=13.5 Hz, 2H), 2.17 (s, 2H), 2.05 (s, 4H), 1.95-1.49 (m, 20H), 1.42 (dd, J=27.1, 14.5 Hz, 5H), 1.28 (s, 2H), 1.25-1.17 (m, 4H), 1.10 (d, J=4.6 Hz, 4H), 1.05-0.79 (m, 18H), 0.78 (d, J=11.9 Hz, 2H). ESI-MS: [M+H]$^+$ 1609.86, $C_{75}H_{113}N_7O_{27}S_2$.

Example 7

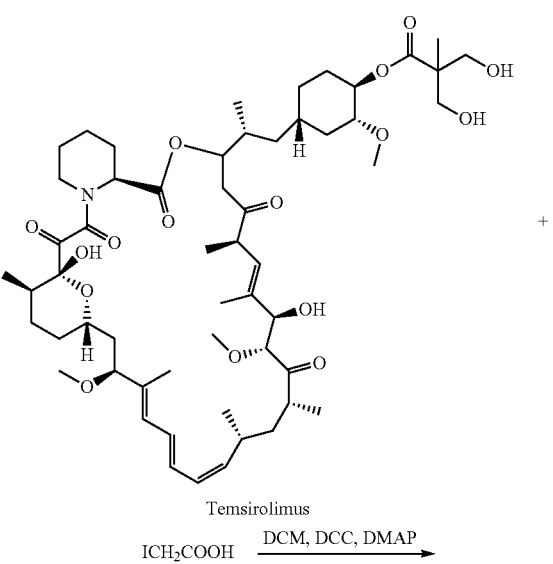

Temsirolimus $ICH_2COOH$ $\xrightarrow{DCM, DCC, DMAP}$

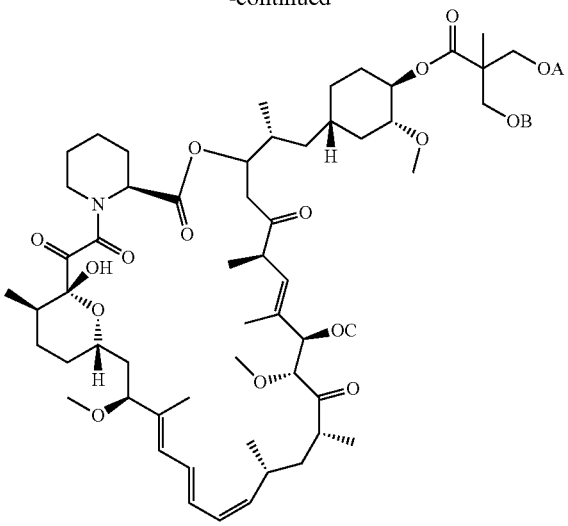

IV-5 A = $COCH_2I$; B = H; C = H;
IV-6 A = $COCH_2I$; B = $COCH_2I$; C = H;
IV-7 A = $COCH_2I$; B = $COCH_2I$; C = $COCH_2I$;

To a 100 mL three-neck flask, temsirolimus (1.2 g, 1.2 mmol) and iodoacetic acid (0.67 g, 3.6 mmol) were added, followed by addition of 10 mL dichloromethane. The mixture was stirred till the solid all dissolved. The mixed mixture was cooled to 0-5° C. and dicyclohexyl carbodiimide (0.74 g, 3.6 mmol) was added, which was stirred at 0-5° C. for 10-15 min. To the reaction mixture 4-dimethylamino pyridine (0.15 g, 1.2 mmol) was added. The reacted mixture was warmed to room temperature and stirred for 16-24 h. Reaction completion of temsirolimus was monitored by TLC, and the insoluble solid was filtrated by a Büchner funnel. The filtrate was concentrated to dry under reduced pressure at 30-40° C. The obtained slurry was purified by silica gel column (eluted with n-hexane/ethyl acetate=10:1-1:1) to obtain temsirolimus monohaloacetate IV-5 (0.31 g, 0.25 mmol), temsirolimus dihaloacetate IV-6 (0.40 g, 0.36 mmol) and temsirolimus trihaloacetate IV-7 (0.36 g, 0.23 mmol), respectively.

Temsirolimus Monohaloacetate IV-5:

$^1$H NMR (400 MHz, $CDCl_3$) δ 6.38 (dt, J=25.1, 14.6 Hz, 1H), 6.16-6.08 (m, 1H), 5.94 (dd, J=28.9, 10.6 Hz, 1H), 5.62-5.48 (m, 1H), 5.42 (d, J=9.9 Hz, 1H), 5.29 (t, J=7.3 Hz, 1H), 5.18 (dt, J=11.8, 5.5 Hz, 1H), 4.36-4.25 (m, 2H), 4.18 (ddd, J=20.8, 14.3, 6.8 Hz, 2H), 3.90-3.78 (m, 2H), 3.76 (d, J=7.4 Hz, 2H), 3.68 (dd, J=14.6, 6.8 Hz, 1H), 3.59 (d, J=13.5 Hz, 1H), 3.45 (d, J=10.3 Hz, 4H), 3.42-3.29 (m, 2H), 3.21-3.06 (m, 7H), 2.86 (dd, J=17.8, 7.2 Hz, 1H), 2.74 (dd, J=16.5, 5.8 Hz, 2H), 2.57 (dd, J=16.6, 6.2 Hz, 1H), 2.30 (d, J=12.9 Hz, 1H), 2.10-1.91 (m, 6H), 1.76 (s, 6H), 1.72-1.58 (m, 8H), 1.54-1.44 (m, 4H), 1.38-1.20 (m, 8H), 1.14 (dd, J=19.8, 6.7 Hz, 4H), 1.06 (d, J=6.5 Hz, 4H), 1.02 (s, 3H), 0.99 (d, J=6.4 Hz, 2H), 0.95 (d, J=6.5 Hz, 2H), 0.93-0.82 (m, 4H), 0.71 (dt, J=16.7, 8.2 Hz, 1H). ESI-MS: [M+NH$_4$]$^+$ 1215.80, $C_{58}H_{88}INO_{17}$.

Temsirolimus Dihaloacetate IV-6:

$^1$H NMR (400 MHz, CDCl$_3$) δ 6.37 (dt, J=24.6, 14.8 Hz, 1H), 6.15-6.09 (m, 1H), 5.95 (dd, J=27.2, 10.6 Hz, 1H), 5.59-5.45 (m, 1H), 5.38 (d, J=9.9 Hz, 1H), 5.25 (t, J=7.2 Hz, 1H), 5.10 (dt, J=11.3, 5.9 Hz, 1H), 4.38-4.29 (m, 2H), 4.12 (m, 2H), 3.88-3.76 (m, 2H), 3.70 (d, J=7.1 Hz, 2H), 3.63 (m, 6H), 3.41 (d, J=10.3 Hz, 4H), 3.38-3.25 (m, 2H), 3.21-3.06 (m, 7H), 2.83 (dd, J=17.8, 7.0 Hz, 1H), 2.77 (dd, J=16.3, 5.5 Hz, 2H), 2.55 (dd, J=16.8, 6.0 Hz, 1H), 2.32 (d, J=12.7 Hz, 1H), 2.14-1.92 (m, 6H), 1.78 (s, 6H), 1.74-1.58 (m, 8H), 1.55-1.39 (m, 4H), 1.39-1.19 (m, 8H), 1.10 (dd, J=182, 6.8 Hz, 4H), 1.06 (d, J=6.6 Hz, 4H), 1.02 (s, 3H), 0.98 (d, J=6.5 Hz, 2H), 0.95 (d, J=6.5 Hz, 2H), 0.90-0.80 (m, 4H), 0.73 (dt, J=16.5, 8.2 Hz, 1H). ESI-MS: [M+NH$_4$]$^+$1383.60, C$_{60}$H$_{89}$I$_2$NO$_{18}$.

Temsirolimus Trihaloacetate IV-7:

$^1$H NMR (400 MHz, CDCl$_3$) δ 6.40 (dt, J=24.8, 14.2 Hz, 1H), 6.16-6.08 (m, 1H), 5.90 (dd, J=28.1, 10.3 Hz, 1H), 5.60-5.48 (m, 1H), 5.40 (d, J=9.9 Hz, 1H), 5.28 (t, J=7.2 Hz, 1H), 5.16 (dt, J=11.6, 5.5 Hz, 1H), 4.35-4.27 (m, 2H), 4.16 (m, 2H), 3.90-3.78 (m, 2H), 3.75 (d, J=7.1 Hz, 2H), 3.68 (dd, J=14.6, 6.8 Hz, 2H), 3.59 (d, J=13.5 Hz, 2H), 3.44 (d, J=10.3 Hz, 4H), 3.43-3.27 (m, 2H), 3.21-3.05 (m, 7H), 2.85 (dd, J=17.7, 7.0 Hz, 1H), 2.74 (dd, J=16.8, 5.5 Hz, 2H), 2.57 (dd, J=16.7, 6.3 Hz, 1H), 2.30 (d, J=12.8 Hz, 1H), 2.12-1.90 (m, 6H), 1.76 (s, 6H), 1.73-1.56 (m, 8H), 1.53-1.40 (m, 4H), 1.38-1.20 (m, 8H), 1.14 (dd, J=19.4, 6.8 Hz, 4H), 1.05 (d, J=6.3 Hz, 4H), 1.01 (s, 3H), 0.99 (d, J=6.5 Hz, 2H), 0.93 (d, J=6.5 Hz, 2H), 0.90-0.81 (m, 4H), 0.70 (dt, J=16.7, 8.0 Hz, 1H). ESI-MS: [M+NH$_4$]$^+$1551.09, C$_{62}$H$_{90}$I$_3$NO$_{19}$.

Example 8

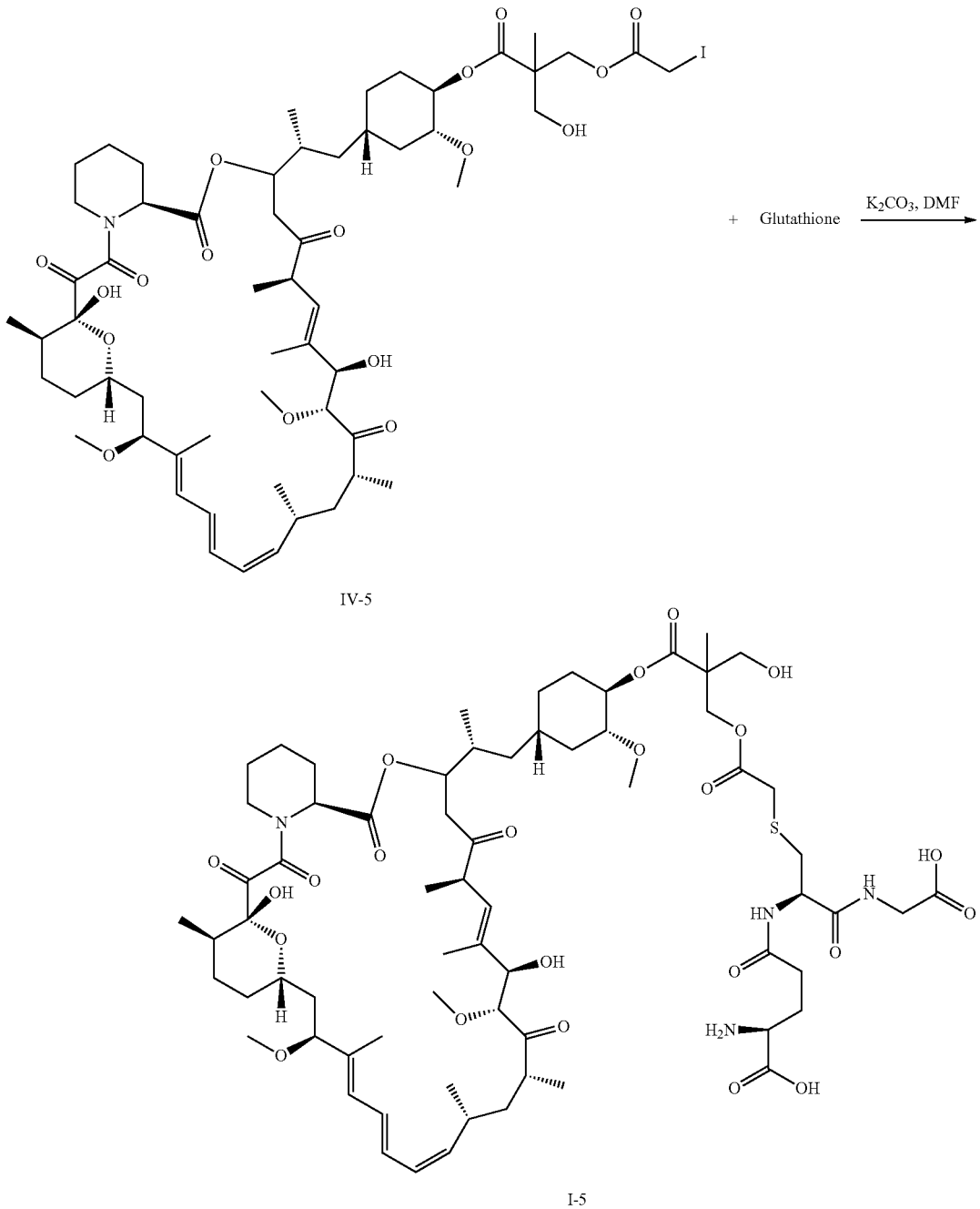

To a 50 mL round bottomed flask, temsirolimus mono-haloacetate IV-5 (0.28 g, 0.23 mmol) and glutathione (0.14 g, 0.46 mmol) were added, followed by addition of 3 mL N,N-dimethylformamide. The mixture was stirred till the solid suspended in the N,N-dimethylformamide. $K_2CO_3$ (19.1 mg, 0.14 mmol) was added to the suspension, to which 3 mL $H_2O$ and 6 mL ethanol were then added. After vigorously stirred for 15 min, the reaction mixture turned clear. The reaction mixture was stirred over night at r.t. Reaction completion of compound IV-5 was monitored by HPLC. The reaction mixture was concentrated to dry under reduced pressure at 45-55° C. The obtained slurry was purified by preparative HPLC to obtain compound I-5 (0.21 g, 0.15 mmol).

compound I-5: $^1$H NMR (400 MHz, $CD_3OD+CDCl_3$) δ 6.47-6.37 (m, 1H), 6.15 (m, 3H), 5.50-5.33 (m, 1H), 5.28 (d, J=10.2 Hz, 1H), 5.12 (s, 2H), 4.66 (s, 1H), 4.23 (d, J=24.0 Hz, 3H), 4.12 (d, J=26.8 Hz, 2H), 3.85 (s, 4H), 3.73-3.50 (m, 3H), 3.49-3.22 (m, 12H), 3.10 (d, J=26.5 Hz, 7H), 2.90 (s, 1H), 2.79 (d, J=17.7 Hz, 1H), 2.52 (dd, J=26.2, 18.0 Hz, 4H), 2.26 (d, J=13.3 Hz, 2H), 2.14 (s, 2H), 2.08 (s, 4H), 1.95-1.52 (m, 16H), 1.45 (dd, J=27.1, 14.5 Hz, 5H), 1.27 (s, 2H), 1.23-1.10 (m, 4H), 1.08 (d, J=4.6 Hz, 4H), 1.05 (s, 3H), 1.01-0.79 (m, 13H), 0.78 (d, J=11.9 Hz, 2H). HR-ESI-MS: [M+H]$^+$ 1378.52, $C_{68}H_{104}N_4O_{23}S$.

Example 9

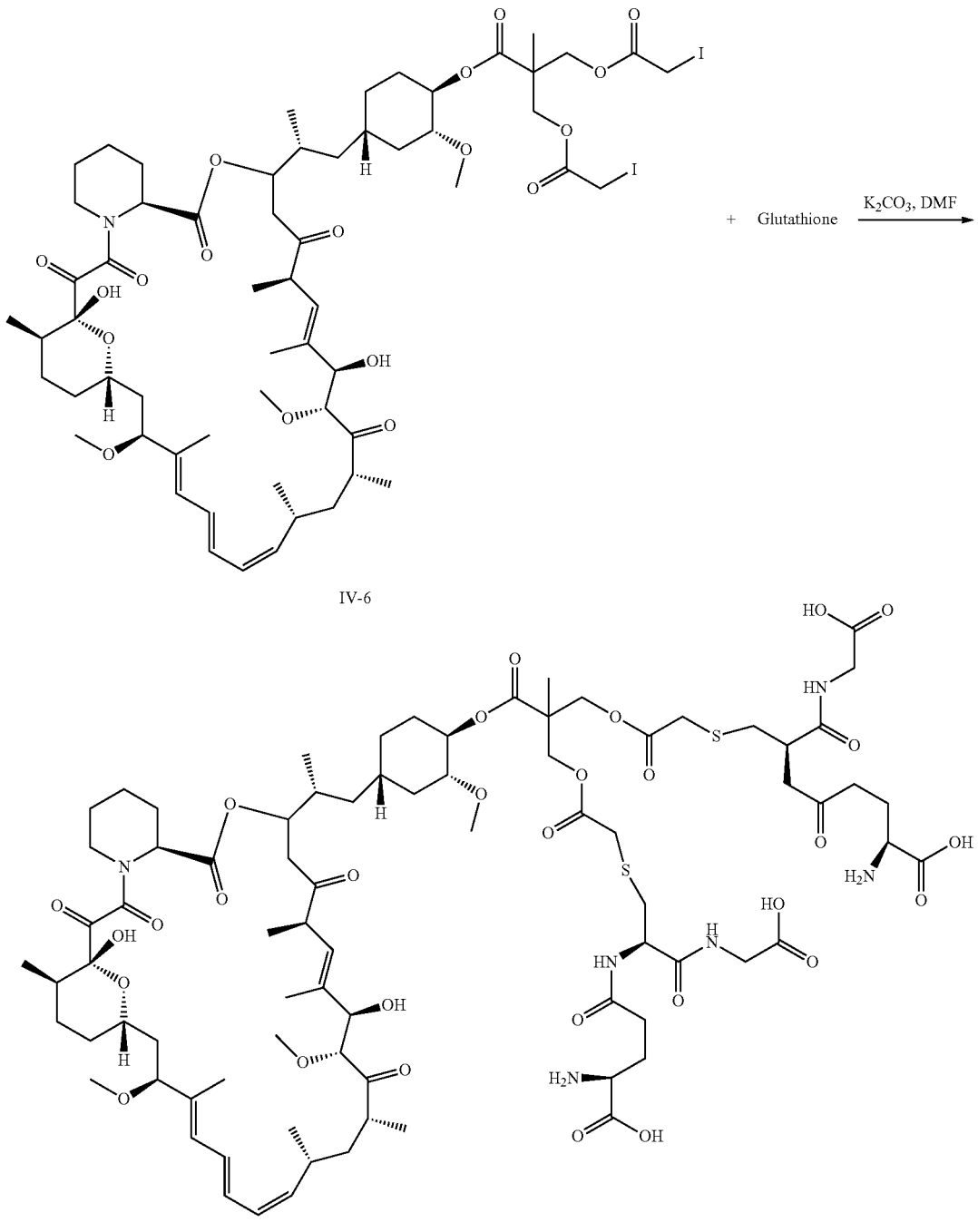

To a 50 mL round bottomed flask, temsirolimus dihaloacetate IV-6 (0.36 g, 0.26 mmol) and glutathione (0.24 g, 0.78 mmol) were added, followed by addition of 3 mL N,N-dimethylformamide. The mixture was stirred till the solid suspended in the N,N-dimethylformamide. $K_2CO_3$ (39.5 mg, 0.29 mmol) was added to the suspension, to which 3 mL $H_2O$ and 6 mL ethanol were then added. After vigorously stirred for 20 min, the reaction mixture turned clear. The reaction mixture was stirred over night at r.t. Reaction completion of compound IV-6 was monitored by HPLC. The reaction mixture was concentrated to dry under reduced pressure at 45-55° C. The obtained residue was purified by preparative HPLC to provide compound I-6 (0.30 g, 0.17 mmol).

compound I-6: $^1$H NMR (400 MHz, $CD_3OD+CDCl_3$) δ 6.49-6.37 (m, 1H), 6.14 (m, 3H), 5.51-5.35 (m, 1H), 5.27 (d, J=10.2 Hz, 1H), 5.07 (s, 2H), 4.60 (s, 1H), 4.20 (d, J=24.3 Hz, 3H), 4.06 (d, J=27.8 Hz, 2H), 3.85 (s, 4H), 3.73-3.48 (m, 8H), 3.45-3.23 (m, 12H), 3.12 (d, J=26.5 Hz, 7H), 2.94 (s, 1H), 2.73 (d, J=17.8 Hz, 1H), 2.54 (dd, J=27.0, 18.2 Hz, 4H), 2.24 (d, J=13.2 Hz, 2H), 2.15 (s, 2H), 2.07 (s, 4H), 1.96-1.50 (m, 16H), 1.45 (dd, J=27.1, 14.5 Hz, 5H), 1.27 (s, 2H), 1.24-1.10 (m, 6H), 1.09 (d, J=4.7 Hz, 4H), 1.05 (s, 3H), 1.05-0.78 (m, 12H), 0.78 (d, J=11.8 Hz, 2H). HR-ESI-MS: $[M+H]^+$ 1725.13, $C_{80}H_{121}N_7O_{30}S_2$.

Example 10

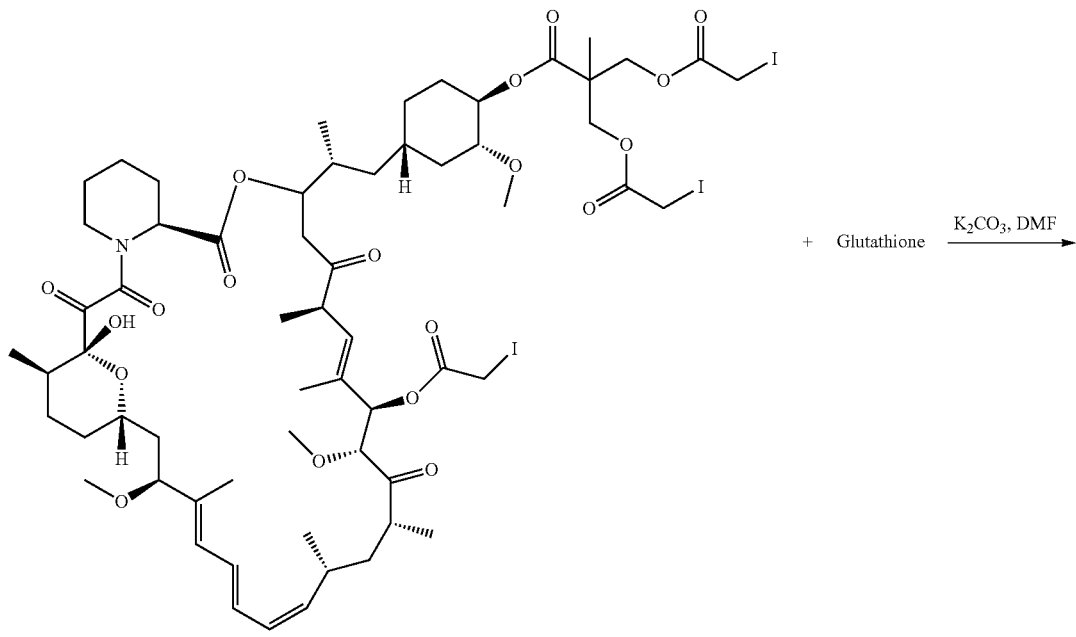

-continued

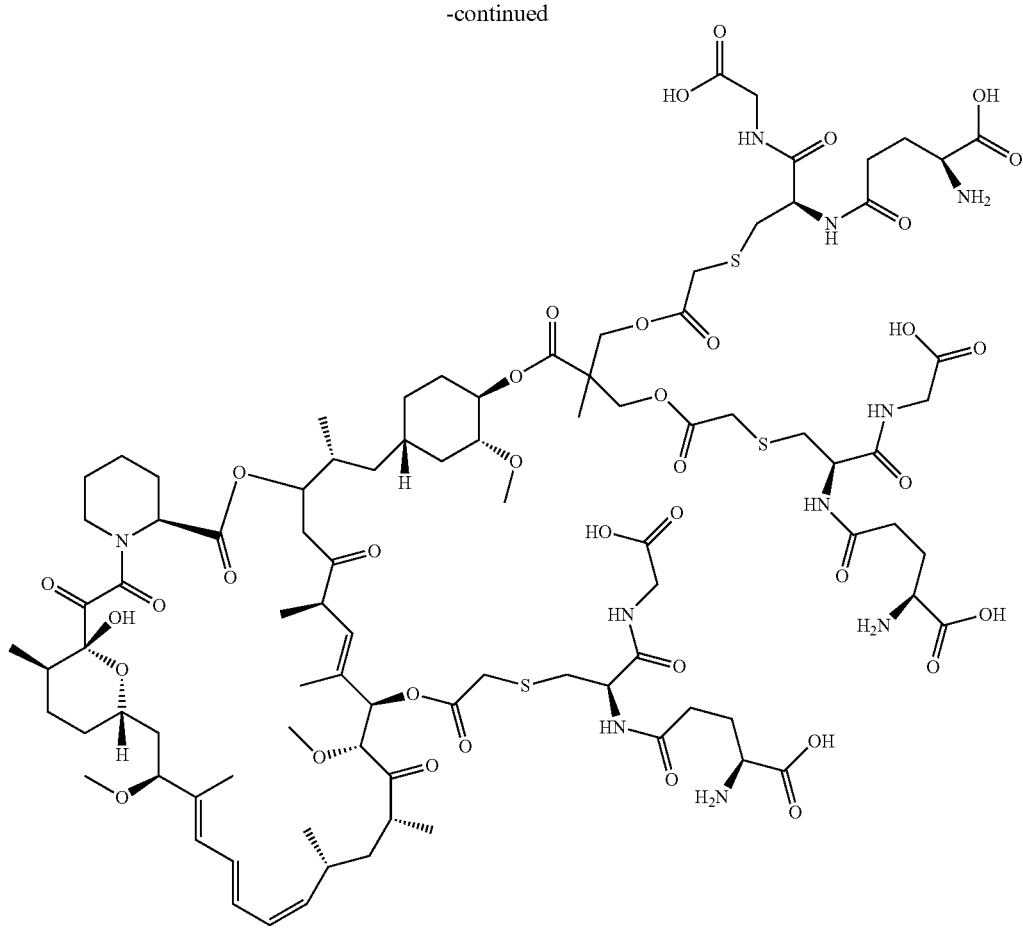

I-7

To a 50 mL round bottomed flask, temsirolimus trihaloacetate IV-7 (0.33 g, 0.22 mmol) and glutathione (0.27 g, 0.88 mmol) were added, followed by addition of 3 mL N,N-dimethylformamide. The mixture was stirred till the solid suspended in the N,N-dimethylformamide. $K_2CO_3$ (60.7 mg, 0.44 mmol) was added to the suspension, to which 3 mL $H_2O$ and 6 mL ethanol were then added. After vigorously stirred for 30 min, the reaction mixture turned clear. The reaction mixture was stirred over night at r.t. Reaction completion of compound IV-7 was monitored by HPLC. The reaction mixture was concentrated to dry under reduced pressure at 45-55° C. The obtained slurry was purified by preparative HPLC to give compound I-7 (0.24 g, 0.12 mmol).

compound I-7: $^1$H NMR (400 MHz, $CD_3OD+CDCl_3$) δ 6.47-6.32 (m, 1H), 6.15 (m, 3H), 5.51-5.35 (m, 1H), 5.21 (d, J=10.0 Hz, 1H), 5.06 (s, 2H), 4.57 (s, 1H), 4.23 (d, J=24.3 Hz, 3H), 4.05 (d, J=27.8 Hz, 2H), 3.86 (s, 4H), 3.73-3.48 (m, 10H), 3.46-3.25 (m, 18H), 3.12 (d, J=26.6 Hz, 7H), 2.95 (s, 1H), 2.78 (d, J=17.1 Hz, 1H), 2.55 (dd, J=27.3, 18.5 Hz, 4H), 2.22 (d, J=13.5 Hz, 2H), 2.12 (s, 2H), 2.03 (s, 4H), 1.93-1.53 (m, 20H), 1.48 (dd, J=27.0, 14.3 Hz, 5H), 1.27 (s, 2H), 1.23-1.14 (m, 8H), 1.09 (d, J=4.6 Hz, 4H), 1.03 (s, 3H), 1.01-0.78 (m, 12H), 0.76 (d, J=11.3 Hz, 2H). HR-ESI-MS: $[M+H]^+$ 2072.30, $C_{92}H_{138}N_{10}O_{37}S_3$.

The following experiments include the methods and results of studying the water solubility and the in vivo and in vitro activity of the specific compounds according to the present invention. Compounds not listed in the following experiments can also be studied using the same method and idea as those used in the following experiments. The following experiments are merely used to illustrate the methods and results of studying the specific compounds according to the present invention, but not to be limited to the compounds used.

Example 11: Test for Solubility in Water

Solubility of the compounds according to the present invention can be confirmed through standard experimental procedure. The experiments herein can measure the dissolution profile in water of the compounds according to the present invention.

The operational procedure used for the solubility test is briefly described by taking compounds I-1 and I-2 as examples.

To a 25 ml volumetric flask, 25 mg everolimus was added, and diluted with acetonitrile to volume. The mixture was shaken till all the solid dissolved, obtaining 1 mg/mL everolimus solution in acetonitrile.

1 mg/mL everolimus solution in acetonitrile was added to a 10 ml volumetric flask, and was diluted with acetonitrile by 2 times, 10 times, 100 times and 1000 times, so as to obtain everolimus solutions in acetonitrile with a concentration of 0.5 mg/mL, 0.1 mg/mL, 0.01 mg/mL and 0.001 mg/mL, respectively.

Standard curve was plotted using peak areas of the main peaks of HPLC with regard to the everolimus solutions with a concentration of 1 mg/mL, 0.5 mg/mL, 0.1 mg/mL, 0.01 mg/mL, 0.001 mg/mL (as shown in FIG. 1), obtaining a linear equation as follow: y=26010x+18.338 ($R^2$=1).

10 mg everolimus, 10 mg compound I-1 and 10 mg compound I-2 were added to three 10 mL volumetric flasks, respectively, and diluted with pure water to volume. Each of the three mixtures was shaken till the solid in the volumetric flask stopped to dissolve. Before analyzed by HPLC, 1 mL of each solution was filtrated via a 0.22 μm filter. The solubility of the compounds was calculated from the standard curve using the peak area of the main peak obtained. Results are shown in Table 1.

TABLE 1

Solubility test results for compounds I-1, I-2 and everolimus

| Compound | Peak area | Solubility in water | Note |
| --- | --- | --- | --- |
| Everolimus | 21 | <0.001 mg/mL | |
| Compound I-1 | 14138 | 0.54 mg/mL | converted to everolimus |
| Compound I-2 | 20896 | 0.80 mg/mL | converted to everolimus |

As shown in table 1, the solubility of compound I-1 in water increases at least 540 times as compared with that of everolimus; and the solubility of compound I-2 in water increases at least 800 times as compared with that of everolimus. Accordingly, the water solubility of compounds modified by glutathione is much higher than that of everolimus.

Based on the same study method, comparisons of the solubility between sirolimus/temsirolimus and the compounds modified by glutathione are carried out, respectively. Results are shown in Table 2 below.

TABLE 2

Solubility test results for compounds I-3, I-4 and sirolimus, and for compounds I-5, I-6, I-7 and temsirolimus

| Compound | Solubility in water | Note |
| --- | --- | --- |
| Sirolimus | <0.001 mg/mL | |
| Compound I-3 | 0.47 mg/L | converted to sirolimus |
| Compound I-4 | 0.61 mg/L | converted to sirolimus |
| Temsirolimus | About 0.001 mg/mL | |
| Compound I-5 | 0.58 mg/mL | converted to temsirolimus |
| Compound I-6 | 0.71 mg/mL | converted to temsirolimus |
| Compound I-7 | 0.83 mg/mL | converted to temsirolimus |

As shown in table 2, the solubility of compound I-3 and 1-4 in water increases at least 470 times and 610 times, respectively, as compared with that of sirolimus; and the solubility of compound I-5, compound I-6 and 1-7 in water increases at least 580 times, 710 times and 830 times, respectively, as compared with that of temsirolimus.

Conclusion: the water solubility of the compounds modified by glutathione according to the present invention is greatly improved as compared with those of the parent compounds before modified, i.e., everolimus, sirolimus and temsirolimus. Therefore, glutathione exhibits significant effect on improving the water solubility of rapamycin compounds.

Example 12: In Vitro Activity Assays

The anti-tumor activity and toxicity of the compounds according to the present invention can be assayed through standard operational procedures of pharmacological experiment. The experiments carried out herein can test the inhibitory effect of the compounds according to the present invention on the growth of human liver cancer cell HepG2, lung cancer cell NCI460, prostate cancer cell DU145, prostate cancer cell PC3, and human breast cancer cell MDA-MB-435. The operational procedure used is briefly described below by taking the inhibitory activity assay against human liver cancer cell HepG2 as an example.

Human liver cancer cell HepG2 grew in the follow medium:

Preparation of the growth medium: BRL minimum essential medium with Earle Salts (500 mL), with the addition of the following agents:

5 mL BRL MEM non-essential amino acids (10 mM);

5 mL BRL penicillin-streptomycin (10000 IU/mL, 10000 μg/mL);

5 mL BRL sodium pyruvate solution (100 mM);

5 mL BRL L-glutamine (200 mM);

50 mL BRL calf serum (qualified).

The growth medium is then obtained and ready for use.

The operational procedure for the assay is as follows:

1. Cells after being trypsinized were inoculated in 96-well plates at a concentration of $10^4$ cells/well, and allowed to grow in a medium with a final volume of 200 μL. The 96-well plates after inoculation are allowed to stand for 24 hours at 37° C., in order to allow the cells to adhere to the surface of the wells.

2. The medium was removed by carefully pipetting without disturbing the cell monolayer. 200 μL Fresh medium was added into each well. It is arranged to make it possible to collect samples from enough wells to run the experiments in triplicate.

3. The compounds to be tested according to the present invention were dissolved into 10 μL phosphate buffered solution (PBS) and incubated for 48 h at 37° C.

4. In the last 6 h of incubation, cells in each well of the 96-well plates were labeled by 1 microcurie T thymidine (New England Nuclear thymidine), by adding 10 μL PBS containing 1 microcurie T thymidine (which was added into the PBS on the day of collecting the samples for test). The 96-well plates were then returned to the incubator and incubated for the last 6 h.

5. Without disturbing the cell monolayer, the radioactive medium was removed by pipetting. Then 50 μL of BRL 10×trypsin was added to each well, followed by incubation at 37° C. for 10 minutes or until the cell monolayer was detached from the bottom (or the wall) of each well. Samples were collected on glass-fiber diskettes using a Skatron 96-well cell harvester. Cells depositing on the glass-fiber diskettes were counted in a Wallac Betaplate counter. The results of in vitro activity tests are shown in Table 3 and Table 5.

TABLE 3

Results of in vitro activity assays for compounds I-1 and I-2

| Cancer cell | Compound I-1 $IC_{50}$ (μM) | Compound I-2 $IC_{50}$ (μM) | Everolimus $IC_{50}$ (μM) |
| --- | --- | --- | --- |
| HepG2 | 11.127 ± 0.005 | 62.032 ± 0.007 | 52.290 ± 0.006 |
| NCI460 | 27.204 ± 0.007 | 100.061 ± 0.009 | 99.811 ± 0.004 |
| DU-145 | 56.215 ± 0.003 | 66.385 ± 0.010 | 57.327 ± 0.005 |
| PC3 | 25.978 ± 0.008 | 35.129 ± 0.008 | 30.270 ± 0.006 |
| MDA-MB-435 | 55.345 ± 0.005 | 65.138 ± 0.004 | 62.570 ± 0.003 |

As it can be seen from Table 3, the inhibitory activities of compound I-1 against the growth of human liver cancer HepG2, lung cancer cell NCI460, prostate cancer cell DU145, prostate cancer cell PC3, and human breast cancer cell MDA-MB-435 are all higher than or equal to those of everolimus. The in vitro inhibitory activity of compound I-2 against cancer cells is equal to or slightly lower than that of everolimus.

TABLE 4

Results of the in vitro activity tests for compounds I-3 and I-4

| Cancer cell | Compound I-3 IC$_{50}$ (µM) | Compound I-4 IC$_{50}$ (µM) | Sirolimus IC$_{50}$ (µM) |
|---|---|---|---|
| HepG2 | 35.188 ± 0.007 | 73.402 ± 0.007 | 66.254 ± 0.007 |
| NCI460 | 82.328 ± 0.011 | 122.801 ± 0.017 | 101.361 ± 0.013 |
| DU-145 | 62.511 ± 0.010 | 93.277 ± 0.011 | 68.520 ± 0.009 |
| PC3 | 31.396 ± 0.008 | 51.413 ± 0.005 | 42.371 ± 0.009 |
| MDA-MB-435 | 63.633 ± 0.015 | 73.283 ± 0.012 | 68.570 ± 0.007 |

As it can be seen from the data of Table 4, the inhibitory activities of compound I-3 against the growth of human liver cancer HepG2, lung cancer cell NCI460, prostate cancer cell DU145, prostate cancer cell PC3, and human breast cancer cell MDA-MB-435 are all higher than or equal to those of sirolimus. The in vitro inhibitory activity of compound I-4 against cancer cells is equal to or slightly lower than that of sirolimus.

TABLE 5

Results of the in vitro activity tests for compound I-5, I-6 and I-7

| | IC$_{50}$ (µM) | | | |
|---|---|---|---|---|
| Cancer cell | Compound I-5 | Compound I-6 | compound I-7 | Temsirolimus |
| HepG2 | 50.213 ± 0.010 | 33.155 ± 0.008 | 76.703 ± 0.012 | 60.337 ± 0.010 |
| NCI460 | 80.530 ± 0.013 | 89.631 ± 0.017 | 131.261 ± 0.010 | 113.255 ± 0.011 |
| DU-145 | 60.813 ± 0.011 | 71.322 ± 0.015 | 82.510 ± 0.015 | 65.361 ± 0.015 |
| PC3 | 38.396 ± 0.008 | 32.991 ± 0.018 | 60.492 ± 0.010 | 47.319 ± 0.005 |
| MDA-MB-435 | 70.761 ± 0.009 | 68.862 ± 0.007 | 81.310 ± 0.008 | 77.310 ± 0.005 |

As it can be seen from the data of Table 5, the inhibitory activities of compound I-5 and 1-6 against the growth of human liver cancer HepG2, lung cancer cell NCI460, prostate cancer cell DU145, prostate cancer cell PC3, and human breast cancer cell MDA-MB-435 are all higher than or equal to those of temsirolimus. The in vitro inhibitory activity of compound I-7 against cancer cells is equal to or slightly lower than that of temsirolimus.

Conclusion: In vitro activity screening experiments indicate that, the compounds modified at only the 42-position of the macrocycle show in vitro inhibitory activities against cancer cells equal to or slightly superior to those of the parent compounds; while the compounds modified at both the 42-position and the 31-position of the macrocycles show in vitro inhibitory activities against cancer cells equal to or slightly lower than those of the parent compounds. Such differences may probably be due to that the binding ability of the compounds to the target is influenced by the modification at the 31-position, resulting in the decrease of the inhibitory activity against cancer cells. However, the inhibitory activity does not decrease dramatically, which may be owing to that the hydroxyl at the 31-position can be released into the culture medium. Based on the above results of the in vitro activity screening experiments, compound I-1 shows the highest in vitro inhibitory activity against cancer cells.

Therefore, more detailed investigations comprising studies on drug release in serum, in vivo activity and in vivo pharmacokinetics were carried out on compound I-1. The following examples 13-17 only show the effects of compound I-1, but according to the contents disclosed in the present invention, by using the same study method with slightly adaptively adjustment according to common knowledge when necessary, the person skilled in the art can reasonably expect that other compounds according to the present invention not listed herein may show test results similar with those of compound I-1.

Example 13: Tests for Drug Release in Serum by Prodrugs

The effects of the compounds according to the present invention as prodrugs of rapamycin can be confirmed by standard operational procedures of pharmacological experiments. The used operational procedures and the obtained results are described briefly below by taking the test for everolimus release of compound I-1 in rats' serum as an example.

10 mL aqueous solution of compound I-1 with a concentration of 1 mg/mL was prepared for use.

10 mL ZnCl$_2$ solution with a concentration of 0.10 mol/L was prepared for use.

1.5 mL blood from ophthalmic artery of rats was injected into a 1.5 mL centrifuge tube and was centrifuged at 12000 rad/min for 10 min. 300 µl supernate (serum) was pipetted into a 1.5 mL centrifuge tube. 7 samples of the serum were prepared for use with the same method.

100 µl aqueous solution of compound I-1 was added to each of centrifuge tubes No. 1-6 filled with the serum. As a blank control, 100 µl water was added to centrifuge tube No. 7. Then the tubes were incubated at 37° C. in an incubator.

300 µl acetonitrile and 300 µl ZnCl$_2$ solution of 0.1 mol/L were added to each of centrifuge tubes No. 1-6 at 10 min, 0.5 h, 1 h, 2 h, 3 h, and 4 h, respectively. The tubes were vortexed homogeneously for 5 min, so as to end the action of the enzyme in the serum on the compounds. 300 µl acetonitrile and 300 µl ZnCl$_2$ solution of 0.1 M were added to the centrifuge tube No. 7 at 4 h, which was then vortexed homogeneously for 5 min.

Figure 2:
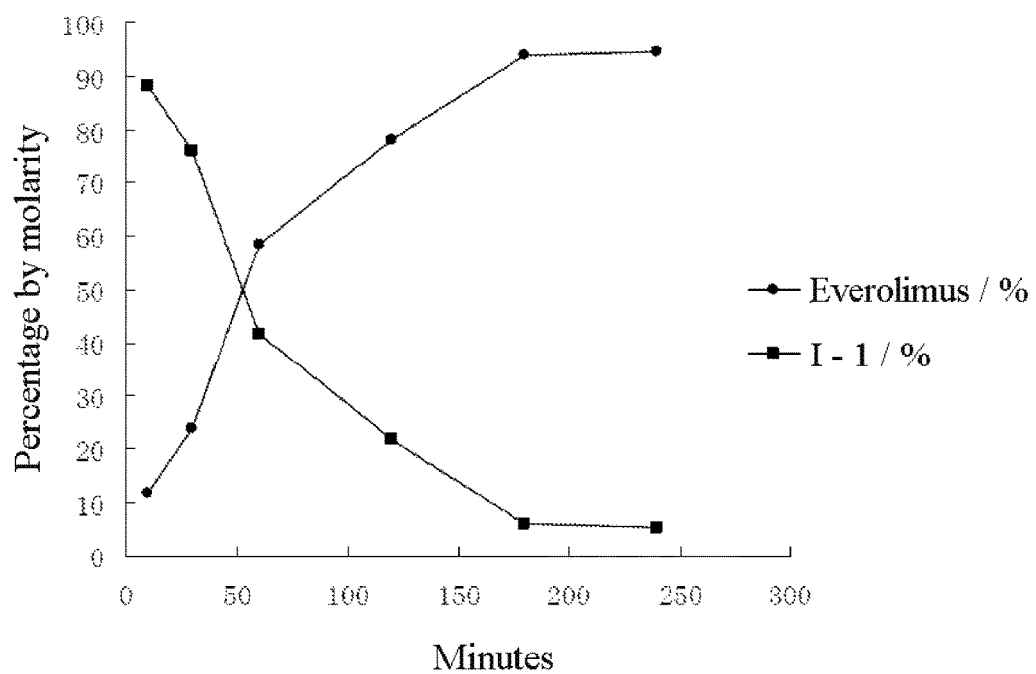
FIG. 2 is a graph showing the test results of everolimus released into the rats' serum by compound I-1 measured in example 13, with percentage of the molar concentration as the vertical coordinate and time with a unit of minute as the horizontal coordinate.

Each of the centrifuge tubes No. 1-7 was centrifuged at 12000 rad/min for 15 min. The protein in the serum was removed via centrifuging. 500 µl supernate from each centrifuge tube was drawn for HPLC, thereby measuring the amounts of everolimus and compound I-1 in the supernate at 10 min, 0.5 h, 1 h, 2 h, 3 h and 4 h, respectively. The test results were shown in FIG. 2.

Conclusion: compound I-1 can slowly release everolimus in rat's serum and substantially release completely in 3 h. Compound I-1 can prolong the action time of everolimus in rats effectively.

Example 14: In Vivo Inhibitory Activity Assays of Compound I-1 Against Tumor in Nude Mice The in vivo anti-tumor activity of the compounds according to the present invention in nude mice can be confirmed by standard operational procedure of pharmacological experiment. The experiment herein can demonstrate the inhibitory effect of the compounds against the growth of cancer cells in animal body. The operational procedure used and the results obtained are briefly described below by taking the test for inhibitory activity against human lung cancer cell NCI-H460 inoculated in the axilla of nude mice as an example. The experimental method is as follows:

NCI-H460 (the $3^{rd}$ generation) tumors in the rapid proliferation stage inoculated in the axilla of nude mice were cut into tumor lumps with a size of 1 mm*1 mm*1 mm and then were inoculated subcutaneously to the right limb of nude mice using a trocar under a sterile condition. When the tumors grew to 150~200 mm$^3$, the mice were divided into groups and then administrated with the compounds for 4 weeks. The major diameter (a) and the minor diameter (b) of the tumors were measured two or three times a week. The tumor volume (TV) and the relative tumor proliferation rate (T/C) were calculated. The equation for calculating the tumor volume is: TV=½×a×b$^2$. The equation for calculating the relative tumor proliferation rate is T/C=TRTC/CRTV (TRTC: average relative tumor volume in the treatment group; CRTV: average relative tumor volume in the vehicle control group). Tumors were stripped and weighted at Day 28 and the tumor-inhibition rate was calculated with the following equation: (tumor weight of control−tumor weight of experimental group)/tumor weight of control×100%.

Grouping method: the mice were divided into 3 groups with 6 mice per group when the tumors averagely grew to about 195 mm$^3$, depending on the growth regularity of the tumor and the dosage regimen. Administration route: intragastrical administration.
G1: Control (vehicle, qw 4×, iv)
G2: Positive drug group: Everolimus (5 mg/kg, qw 4×, iv)
G3: compound I-1 (6.8 mg/kg, qw 4×, iv) (compound I-1 and everolimus were administrated in an equimolar dosage, i.e., 6.8 mg of compound I-1 equivalent to 5 mg of everolimus)

Figure 3:
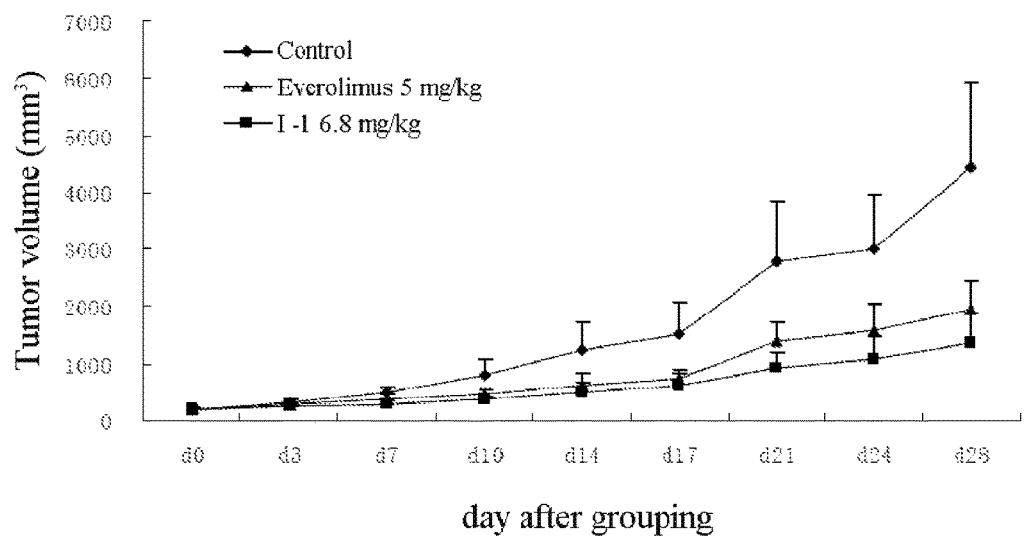
FIG. 3 is a graph showing the growth trends of volume of NCI-460 tumor in nude mice measured in example 14.
Figure 4:
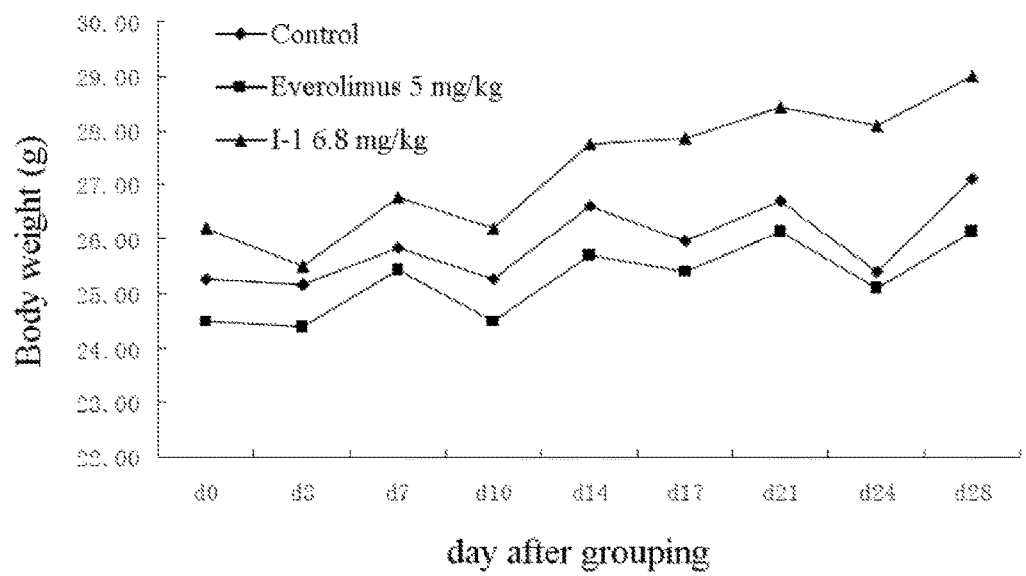
FIG. 4 is a graph showing the variation trends of body weight of nude mice measured in example 14.
Figure 5:
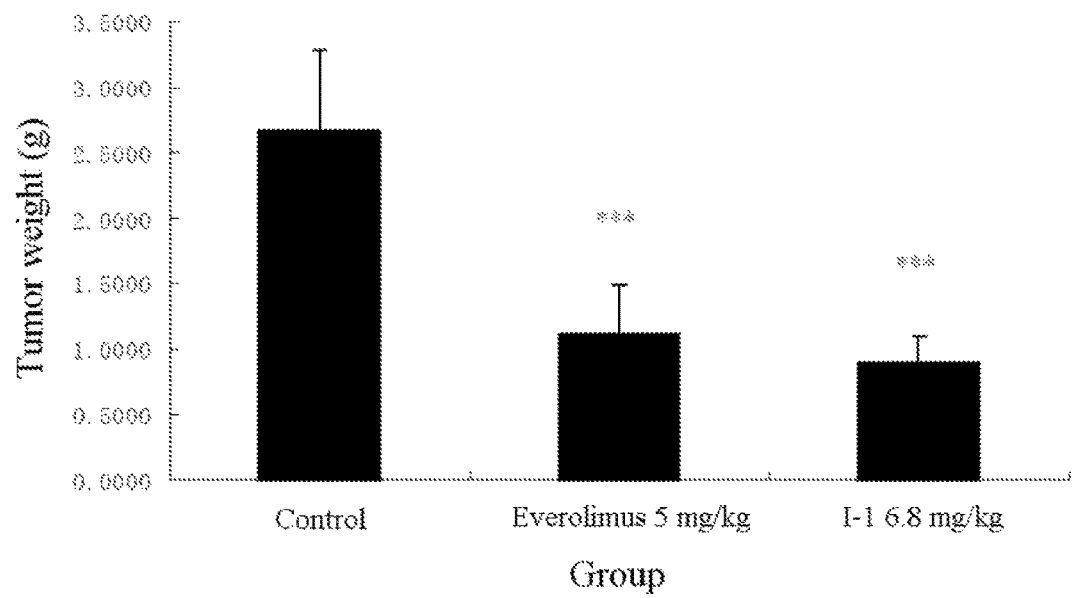
FIG. 5 shows the NCI-460 tumor weights in nude mice measured in example 14.

The test results are shown in Tables 6-8 and FIGS. 3 to 5.
1. Variation in Tumor Volumes

TABLE 6

Variation in tumor volumes

Mean Volume of Tumor (mm$^3$) ± SD n = 6

| Group | | Day 0 | Day 3 | Day 7 | Day 10 | Day 14 | Day 17 | Day 21 | Day 24 | Day 28 |
|---|---|---|---|---|---|---|---|---|---|---|
| G1 | Mean value | 195.4066 | 305.0651 | 497.7840 | 799.0468 | 1254.2091 | 1530.1968 | 2783.1412 | 3017.2579 | 4440.9582 |
| | SD | 16.0770 | 56.8287 | 95.0110 | 295.8187 | 472.1408 | 550.9210 | 1070.2739 | 961.8812 | 1497.1678 |
| | CRTV | | 1.5612 | 2.5474 | 4.0891 | 6.4185 | 7.8308 | 14.2428 | 15.4409 | 22.7268 |
| G2 | Mean value | 194.8659 | 264.7517 | 356.6133 | 457.1105 | 626.5192 | 730.3766 | 1386.2102 | 1593.5901 | 1955.7073 |
| | SD | 14.5571 | 32.8797 | 94.0622 | 110.8942 | 198.6940 | 180.6408 | 336.3916 | 442.0834 | 501.8338 |
| | TRTV | | 1.3586 | 1.8300 | 2.3458 | 3.2151 | 3.7481 | 6.6005 | 7.1515 | 9.5230 |
| | T/C (%) | | 0.8703 | 0.7184 | 0.5737 | 0.5009 | 0.4786 | 0.4634 | 0.4632 | 0.4190 |
| | p | | 0.1635 | 0.0271 | 0.0243 | 0.0133 | 0.0070 | 0.0085 | 0.0037 | 0.0025 |
| G3 | Mean value | 195.1545 | 232.4297 | 273.2138 | 360.0897 | 506.8288 | 612.8810 | 934.2806 | 1089.1761 | 1354.8457 |
| | SD | 15.1079 | 13.3489 | 74.5116 | 57.7922 | 166.7389 | 227.9599 | 280.5590 | 396.2484 | 547.8369 |
| | TRTV | | 1.1910 | 1.4000 | 1.8452 | 2.5971 | 3.1405 | 5.2998 | 6.0935 | 7.9673 |
| | T/C (%) | | 0.7629 | 0.5496 | 0.4512 | 0.4046 | 0.4010 | 0.3721 | 0.3946 | 0.3506 |
| | p | | 0.0123 | 0.0010 | 0.0051 | 0.0044 | 0.0037 | 0.0031 | 0.0016 | 0.0013 |

As it can be seen from the data of Table 6 and the increase curve of tumor volume in nude mice shown in FIG. 3, on Day 28, compound I-1 shows a notable inhibitory effect against NCI-H460 in nude mice, with a T/C value of 35% (lower than 40%), while an equimolar amount of everolimus shows a T/C value of 42% (higher than 40%) against NCI-H460 in nude mice. Thus, the inhibitory effect against tumor of the compound I-1 group is superior to that of the everolimus group.

2. Variation in Body Weight of Nude Mice

TABLE 7

Variation in body weight of nude mice

Body Weights (g) n = 6

| Group | | Day 0 | Day 3 | Day 7 | Day 10 | Day 14 | Day 17 | Day 21 | Day 24 | Day 28 |
|---|---|---|---|---|---|---|---|---|---|---|
| G1 | Mean value | 25.28 | 25.15 | 25.84 | 25.28 | 26.62 | 25.97 | 26.69 | 25.39 | 27.10 |
| | SD | 0.85 | 1.57 | 1.43 | 0.85 | 2.13 | 2.14 | 2.91 | 2.44 | 2.39 |
| | Decrease in body weight | | 0.13 | −0.56 | 0.00 | −1.34 | −0.70 | −1.42 | −0.12 | −1.83 |
| | Decrease rate | | 0.51% | −2.24% | 0.00% | −5.31% | −2.76% | −5.60% | −0.47% | −7.23% |

TABLE 7-continued

Variation in body weight of nude mice

| Group | | Day 0 | Day 3 | Day 7 | Day 10 | Day 14 | Day 17 | Day 21 | Day 24 | Day 28 |
|---|---|---|---|---|---|---|---|---|---|---|
| G2 | Mean value | 24.50 | 24.38 | 25.44 | 24.50 | 25.68 | 25.39 | 26.13 | 25.09 | 26.14 |
| | SD | 1.85 | 2.08 | 1.92 | 1.85 | 2.00 | 1.59 | 1.58 | 1.54 | 1.54 |
| | Decrease in body weight | | 0.13 | −0.94 | 0.00 | −1.18 | −0.89 | −1.63 | −0.59 | −1.64 |
| | Decrease rate | | 0.51% | −3.82% | 0.00% | −4.83% | −3.63% | −6.65% | −2.41% | −6.67% |
| G3 | Mean value | 26.20 | 25.49 | 26.79 | 26.20 | 27.74 | 27.84 | 28.42 | 28.09 | 29.00 |
| | SD | 1.09 | 1.13 | 0.76 | 1.09 | 1.20 | 1.03 | 1.11 | 0.95 | 0.14 |
| | Decrease in body weight | | 0.72 | −0.58 | 0.00 | −1.54 | −1.64 | −2.22 | −1.89 | −2.80 |
| | Decrease rate | | 2.73% | −2.23% | 0.00% | −5.87% | −6.24% | −8.46% | −7.20% | −10.68% |

The decrease in body weight can indirectly indicate the toxic and side effect of the drugs on animals. It can be seen from the data in Table 7 and the variation trends of body weight of nude mice shown in FIG. 4, the increase in body weight of compound I-1 group (group G3) is larger than that of the control and the positive drug (everolimus) groups (group G1 and G2), while the increase in body weight of the positive drug (everolimus) groups is less than that of the control. Therefore, the toxic and side effect in vivo of compound I-1 is significantly lower than that of everolimus.

3. Tumor Weight and Tumor Inhibition Rate

TABLE 8

Tumor Weight and tumor inhibition rate

| Group | Tumor Weight(g) ± SD | Tumor Inhibition rate (%) |
|---|---|---|
| Control | 2.6691 ± 0.6117 | |
| Everolimus 5 mg/kg | 1.1741 ± 0.3687 | 56.01% |
| Compound I-1 6.8 mg/kg | 0.8463 ± 0.1582 | 68.29% |

The data in Table 8 and the tumor weight in nude rat and the tumor inhibition rate shown in FIG. 5 indicate that the tumor inhibition rate of compound I-1 in nude rate is significantly superior to that of everolimus.

Conclusion: At the end of the experiment, the data from the NCI-H460 inoculated nude mice model indicate that: the compound I-1 group is the effective dosage group, which shows a T/C value of lower than 40% (35%) and a tumor inhibition rate of higher than 60% (68%), showing a good inhibitory effect against tumors formed by inoculating NCI-H460 cells; The positive drug (everolimus) group shows a T/C value of higher than 40% (42%) and a tumor inhibition rate of lower than 60% (56%). The in vivo inhibitory activity of compound I-1 against NCI-H460 cells is significantly superior to that of everolimus; and the increase in body weight of the compound I-1 group (group G3) is significantly higher than that of the positive drug (everolimus) group (group G2). The toxic and side effect of compound I-1 in animal body is significantly lower than that of the everolimus.

Example 15: Comparative Study on the In Vivo Tumor Inhibitory Efficacy of Compound I-1 Via Intragastrical Administration and Injection Administration The anti-tumor activity of the compounds according to the present invention in nude mice can be confirmed by standard operational procedures of pharmacological experiment. Such experiment can demonstrate the inhibitory effect of the compounds according to the present invention against the growth of cancer cells in animal body.

DU145 (the $3^{rd}$ generation) tumors in the rapid proliferation stage inoculated in the axilla of nude mice were cut into tumor lumps with a size of 1 mm*1 mm*1 mm and then were inoculated subcutaneously to the right limb of nude mice using a trocar under a sterile condition. When the tumors grow to 150-200 mm$^3$, the mice were randomly divided into three groups and then administrated with the compounds for 4 weeks. The major diameter (a) and the minor diameter (b) of the tumors were measured 2 or 3 times a week. The tumor volume (TV) was calculated with the following equation: TV=½×a×b$^2$. Tumors were stripped and weighted at Day 28 and the tumor inhibition rate was calculated using the following equation: (tumor weight of control−tumor weight of experimental group)/tumor weight of control×100%.

The nude mice were divided into 3 groups with 4 mice per group when the tumors averagely grew to about 185-200 mm$^3$, depending on the growth regularity of the tumor and the dosage regimen.

G1: positive drug group: Everolimus (5 mg/kg, qw, 4 w, 3×/w); administration route: intragastrical administration;

G2: compound I-1 (3.4 mg/kg, qw, 4 w, 3×/w) (3.4 mg of compound I-1 equivalent to 2.5 mg of everolimus); administration route: tail vein injection;

G3: compound I-1 (1.7 mg/kg, qw, 4 w, 3×/w) (1.7 mg of compound I-1 equivalent to 1.25 mg of everolimus); administration route: tail vein injection.

Figure 6:
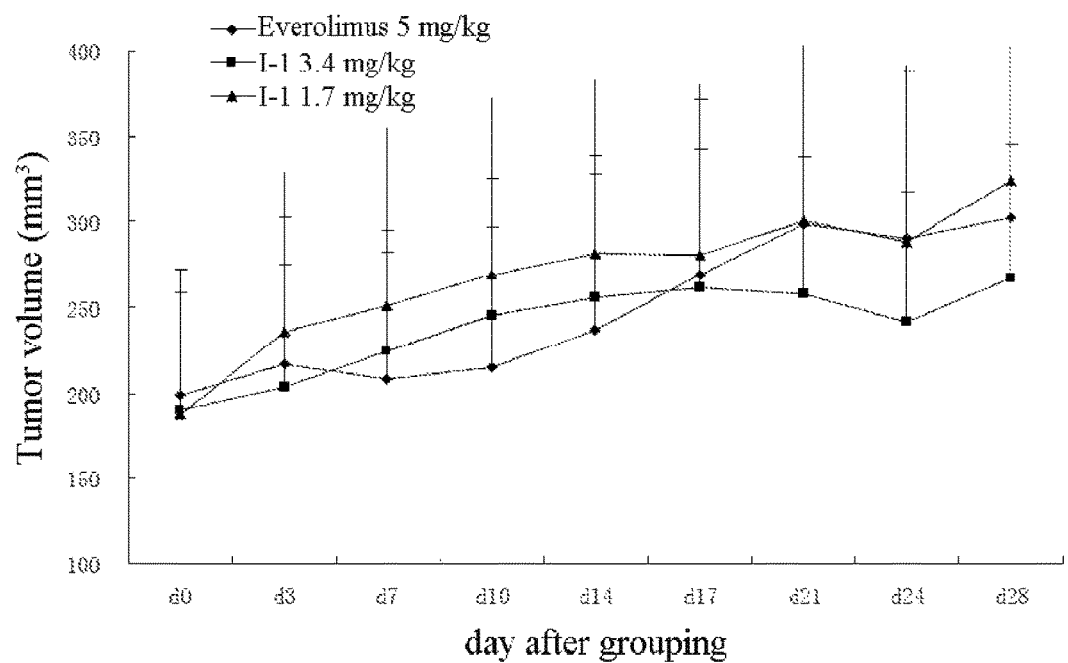
FIG. 6 is a graph showing the growth trends of volume of DU145 tumor in nude mice measured in example 15.

The test results are shown in Tables 9 to 10 and FIG. 6:

1. Variation in Tumor Volumes

TABLE 9

Variation in tumor volumes

| Group | | Day 0 | Day 3 | Day 7 | Day 10 | Day 14 | Day 17 | Day 21 | Day 24 | Day 28 |
|---|---|---|---|---|---|---|---|---|---|---|
| G1 | Mean Value | 198.71 | 216.57 | 208.07 | 215.24 | 236.94 | 268.62 | 298.50 | 289.57 | 302.22 |
| | SD | 146.91 | 171.30 | 147.55 | 162.36 | 181.57 | 205.91 | 236.55 | 196.74 | 245.02 |

TABLE 9-continued

Variation in tumor volumes

Mean Volume of Tumor (mm³) ± SD n = 4

| Group | | Day 0 | Day 3 | Day 7 | Day 10 | Day 14 | Day 17 | Day 21 | Day 24 | Day 28 |
|---|---|---|---|---|---|---|---|---|---|---|
| G2 | Mean Value | 189.84 | 203.79 | 223.91 | 245.45 | 255.59 | 261.55 | 257.96 | 241.11 | 267.54 |
|    | SD | 136.84 | 142.72 | 141.50 | 158.89 | 165.81 | 160.27 | 158.44 | 151.69 | 155.38 |
| G3 | Mean Value | 187.29 | 235.34 | 250.90 | 269.25 | 281.22 | 280.18 | 300.52 | 288.39 | 323.75 |
|    | SD | 134.00 | 186.16 | 206.19 | 206.95 | 203.15 | 199.61 | 214.18 | 206.09 | 205.51 |

As it can be seen from the data in the above Table 9 and the increase trend of tumor volume shown in FIG. 6, at the end of the test, tail-vain-injection administration of compound I-1 in a dosage equivalent to a quarter of that of everolimus can achieve substantially the same tumor inhibitory effect as that of intragastrical administration of everolimus; tail-vain-injection administration of compound I-1 in a dosage equivalent to half of that of everolimus can achieve a tumor inhibitory effect significantly superior to that of intragastric administration of everolimus.

2. Variation in Body Weight of Nude Mice

TABLE 10

Variation in body weight of nude mice

Body Weight (g) n = 4

| Group | | Day 0 | Day 3 | Day 7 | Day 10 | Day 14 | Day 17 | Day 21 | Day 24 | Day 28 |
|---|---|---|---|---|---|---|---|---|---|---|
| G1 | Mean Value | 24.36 | 24.68 | 24.99 | 24.93 | 24.94 | 25.88 | 25.27 | 25.33 | 25.31 |
|    | SD | 1.83 | 2.11 | 2.16 | 2.09 | 2.73 | 2.18 | 2.46 | 2.19 | 1.89 |
|    | SEM | 0.91 | 1.05 | 1.08 | 1.05 | 1.37 | 1.09 | 1.23 | 1.09 | 0.94 |
|    | Decrease in body weight | | −0.32 | −0.63 | −0.57 | −0.58 | −1.52 | −0.91 | −0.97 | −0.95 |
|    | Decrease rate | | −1.32% | −2.59% | −2.32% | −2.38% | −6.24% | −3.75% | −3.96% | −3.90% |
| G2 | Mean Value | 25.30 | 25.92 | 26.13 | 26.15 | 26.59 | 26.34 | 26.84 | 26.58 | 26.96 |
|    | SD | 1.90 | 2.29 | 2.17 | 2.39 | 2.18 | 2.30 | 2.09 | 2.29 | 2.14 |
|    | SEM | 0.95 | 1.14 | 1.09 | 1.20 | 1.09 | 1.15 | 1.05 | 1.14 | 1.07 |
|    | Decrease in body weight | | −0.62 | −0.83 | −0.85 | −1.30 | −1.04 | −1.54 | −1.29 | −1.66 |
|    | Decrease rate | | −2.45% | −3.29% | −3.37% | −5.12% | −4.12% | −6.09% | −5.08% | −6.57% |
| G3 | Mean Value | 26.86 | 27.32 | 27.17 | 27.18 | 27.69 | 27.81 | 28.10 | 28.12 | 28.27 |
|    | SD | 1.56 | 1.16 | 1.82 | 2.15 | 1.55 | 1.47 | 1.39 | 1.31 | 0.95 |
|    | SEM | 0.78 | 0.58 | 0.91 | 1.08 | 0.78 | 0.73 | 0.69 | 0.66 | 0.47 |
|    | Decrease in body weight | | −0.46 | −0.31 | −0.32 | −0.83 | −0.95 | −1.24 | −1.26 | −1.41 |
|    | Decrease rate | | −1.70% | −1.16% | −1.18% | −3.10% | −3.54% | −4.61% | −4.68% | −5.26% |

The decrease in body weight can indirectly indicate the toxic and side effect of the drugs on animals. It can be seen from the data in Table 10 that: the increase trend of body weight of the injection administration groups (group G2 and G3) is larger than that of the intragastrical administration group (group G1). Therefore, injection administration of compound I-1 does not result in obvious toxic and side effect.

Conclusion: The water solubility of compound I-1 is significantly improved. Compound I-1 can be dissolved in normal saline and the resulted solution is stable. Thus, the bioavailability of the compound in vivo can be significantly enhanced via injection administration. The test results indicate that injection administration of compound I-1 in a dosage equivalent to a quarter of that of everolimus can achieve the same tumor inhibitory effect as that of intragastrical administration of everolimus.

Example 16: In Vivo Inhibitory Activity Assays of Compound I-1 Against Human Renal Cell Carcinoma OS-RC-2 in Nude Mice OS-RC-2 (the $3^{rd}$ to $10^{th}$ generation) tumors in the rapid proliferation stage inoculated in the axilla of nude mice were cut into tumor lumps with a size of 1 mm*1 mm*1 mm and then were inoculated subcutaneously to the right limb of nude mice using a trocar under a sterile condition. When the tumors grew to 167 mm³, the mice were randomly divided into groups and administrated with the compounds. The major diameter (a) and the minor diameter (b) of the tumors were measured 2 or 3 times a week. The tumor volume (TV) was calculated with the following equation: TV=½×a×b².

The experiment was terminated and tumors were stripped and weighted. The tumor inhibition rate was calculated.

Grouping method: the mice were divided into 7 groups with 6 mice per group when the tumors averagely grew to 167 mm³:
1) G1: control (vehicle);
2) G2: everolimus (2 mg/kg ig 3×/qw);
3) G3: everolimus (6 mg/kg ig 3×/qw);
4) G4: compound I-1 (8.12 mg/kg ig 3×/qw) (compound I-1 and group G3 of everolimus were administrated in an equimolar dosage, i.e., 8.12 mg of compound I-1 equivalent to 6 mg of everolimus);
5) G5: compound I-1 (2.0 mg/kg iv 3×/qw) (2.0 mg of compound I-1 equivalent to 1.5 mg of everolimus);
6) G6: compound I-1 (8.12 mg/kg iv 3×/qw) (8.12 mg of compound I-1 equivalent to 6 mg of everolimus)
7) G7: compound I-1 (32.7 mg/kg iv 1×/qw) (32.74 mg of compound I-1 equivalent to 24 mg of everolimus).

Figure 7:
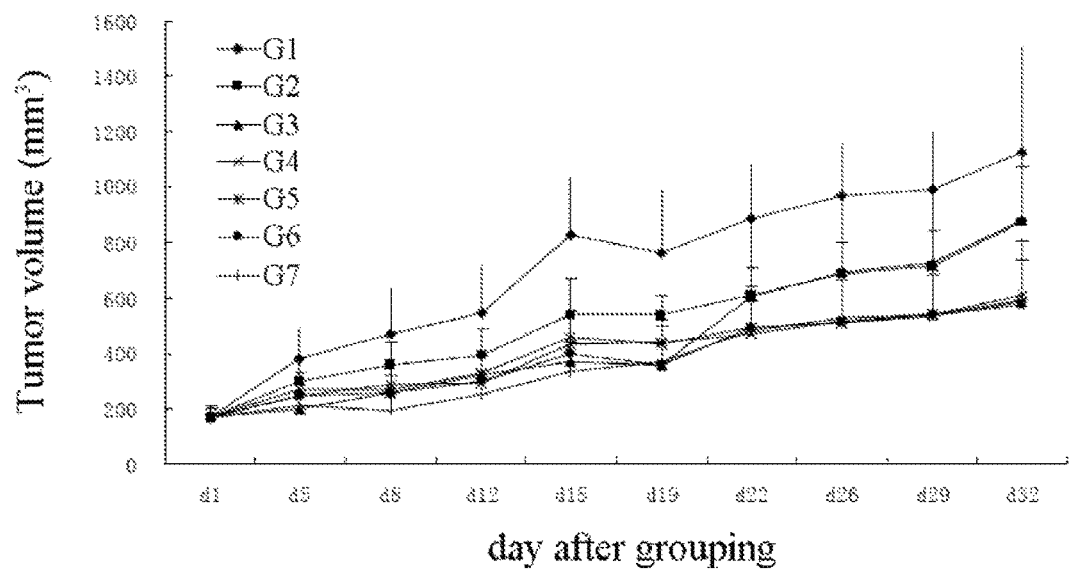
FIG. 7 is a graph showing the growth trends of volumes of human renal cell carcinoma OS-RC-2 in nude mice measured in example 16.
Figure 8:
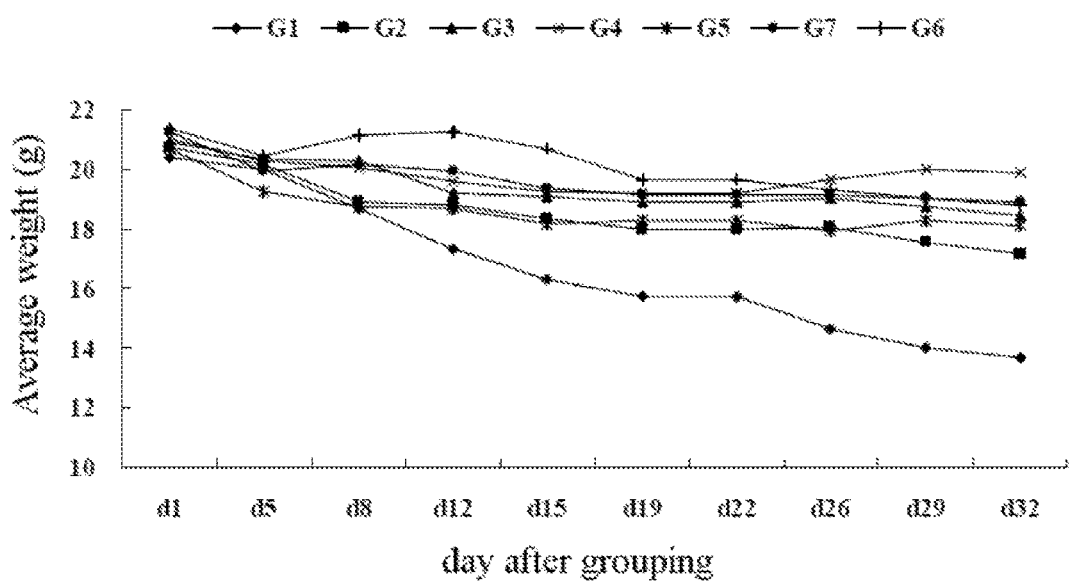
FIG. 8 is a graph showing the variation trends of body weight of nude mice measured in example 16.

The test results are shown in Tables 11, 12 and FIGS. 7 and 8.

1. Tumor Weights and Tumor Inhibition Rate in Nude Mice

TABLE 11

Tumor weight and tumor inhibition rate

| Group | Tumor Weight(g) ± SD | P | Tumor Inhibition Rate (%) |
|---|---|---|---|
| G1 | 0.6767 ± 0.1476 | | |
| G2 | 0.4360 ± 0.0.1294 | 0.0133 | 35.6% |
| G3 | 0.4093 ± 0.3863 | 0.0121 | 41.1% |
| G4 | 0.3002 ± 0.1108 | 0.0005 | 55.6% |
| G5 | 0.2905 ± 0.0936 | 0.0003 | 57.1% |
| G6 | 0.2710 ± 0.1695 | 0.0013 | 59.9% |
| G7 | 0.2669 ± 0.1023 | 0.0002 | 60.6% |

As it can be seen from the increase trend of the tumor volumes in nude mice shown in FIG. 7, for the nude mice which were administrated with everolimus orally three times a week (Group G2 and G3), neither the high-dose group of 6 mg/Kg nor the low-dose group of 2 mg/Kg can effectively inhibit the increase of tumor volumes in nude mice after 32 days; while for the compound I-1 groups via injection administration (Groups G5, G6 and G7), either a low-dose administration (2.0 mg/Kg) 3 times a week or a high-dose administration (32.7 mg/Kg) once a week shows a good tumor inhibitory effect.

The final weight of the tumors in nude mice and the calculated tumor inhibition rate shown in Table 11 further indicate that, either a low-dose injection administration or a high-dose injection administration of compound I-1 (groups G5, G6 and G7) shows a good tumor inhibitory effect, with a tumor inhibitory rate of 57.1%, 59.9% and 60.6%, respectively, which are all significantly superior to that of the everolimus groups (group G2 and G3). Among others, the high-dose injection administration of compound I-1 once a week shows the best effect, with a tumor inhibition rate of up to 60.6%. Meanwhile, even if compound I-1 is administrated in an equimolar dosage of everolimus via the same administration route, the tumor inhibition rate of compound I-1 is significantly higher than that of everolimus (comparing G4 with G3, the tumor inhibition rate is 55.6% and 41.1%, respectively).

2. Variation in Body Weight of Nude Mice

The body weight can indirectly reflect the toxicity of the drugs. The data in Table 12 and FIG. 8 show that the body weight of the nude mice in the blank control decreases greatly with a decrease rate of up to 33.0%. Such situation may be probably due to the nutritional deficiency caused by the growth of the tumor. Moreover, the decrease rate of body weight in the drug treatment group is lower than that in the blank control. Among others, the high-dose compound I-1 groups (groups G6 and G7) show a decrease rate in body weight of 11.7% and 10.7%, respectively; while the everolimus groups via oral administration (groups G2 and G3) show a decrease rate in body weight of 17.4% and 11.7%, respectively. Comparing with the everolimus groups via oral administration, the high-dose compound I-1 group does not show a notable toxicity. Thus, the mice show a good tolerance for the high-dose compound I-1 via injection administration. And no notable toxic effect was observed.

Conclusion: Via the high-dose administration of compound I-1 once weekly, the growth of renal cell carcinoma in nude mice can be inhibited effectively, with a tumor inhibition rate of up to 60.6%; while the everolimus group via oral administration of 6 mg/kg three times a week provides a tumor inhibition rate of only 41.1% in nude mice. The administration by injection once weekly can raise the treatment compliance of the advanced cancer patients on clinic. And the mice show a relative good tolerance for the high-dose compound I-1 via injection administration. No notable toxic effect was observed.

Example 17: In Vivo Pharmacokinetic Study of Compound I-1 in Rats

To further study the in vivo pharmacokinetic characteristics of compound I-1 in rats, compound I-1 was administrated to SD rats via intravenous injection. The in vivo pharmacokinetic characteristics and bioavailability of everolimus released in rats were measured, and compared with the pharmacokinetic characteristics of everolimus via oral administration. The administration route and sampling frequency are shown in the following Table 13.

TABLE 12

Variation in body weight of nude mice

| | | Body Weight (g)n = 6 | | | | | | | | |
|---|---|---|---|---|---|---|---|---|---|---|
| Group | | Day 1 | Day 5 | Day 8 | Day 12 | Day 15 | Day 19 | Day 22 | Day 26 | Day 29 | Day 32 |
| G1 | Mean Value | 20.40 | 20.00 | 18.66 | 17.33 | 16.28 | 15.69 | 15.69 | 14.65 | 14.03 | 13.68 |
| | Decrease rate of body weight | | 1.9% | 8.5% | 15.0% | 20.2% | 23.1% | 23.1% | 28.2% | 31.2% | 33.0% |
| G2 | Mean Value | 20.76 | 20.16 | 18.92 | 18.81 | 18.33 | 17.98 | 17.98 | 18.05 | 17.53 | 17.14 |
| | Decrease rate of body weight | | 2.9% | 8.9% | 9.4% | 11.7% | 13.4% | 13.4% | 13.0% | 15.6% | 17.4% |
| G3 | Mean Value | 20.94 | 20.37 | 20.29 | 19.23 | 19.11 | 18.90 | 18.90 | 19.03 | 18.74 | 18.48 |
| | Decrease rate of body weight | | 2.7% | 3.1% | 8.2% | 8.7% | 9.7% | 9.7% | 9.1% | 10.5% | 11.7% |
| G4 | Mean Value | 21.04 | 20.27 | 20.04 | 19.62 | 19.29 | 19.19 | 19.19 | 19.65 | 20.02 | 19.87 |
| | Decrease rate of body weight | | 3.7% | 4.8% | 6.7% | 8.3% | 8.8% | 8.8% | 6.6% | 4.8% | 5.6% |
| G5 | Mean Value | 20.67 | 19.27 | 18.76 | 18.71 | 18.18 | 18.30 | 18.30 | 17.95 | 18.29 | 18.12 |
| | Decrease rate of body weight | | 6.8% | 9.2% | 9.5% | 12.0% | 11.5% | 11.5% | 13.1% | 11.5% | 12.3% |
| G6 | Mean Value | 21.39 | 20.46 | 21.16 | 21.25 | 20.71 | 19.67 | 19.67 | 19.31 | 19.04 | 18.80 |
| | Decrease rate of body weight | | 4.4% | 1.1% | 0.7% | 3.2% | 8.0% | 8.0% | 9.7% | 10.5% | 11.7% |
| G7 | Mean Value | 21.28 | 19.97 | 20.14 | 19.93 | 19.38 | 19.12 | 19.12 | 19.12 | 19.04 | 18.94 |
| | Decrease rate of body weight | | 6.2% | 5.3% | 6.3% | 8.9% | 10.2% | 10.2% | 10.2% | 10.5% | 10.7% |

TABLE 13

Comparative study of in vivo pharmacokinetics
of compound I-1 in rats via injection administration

| Sample | Sampling | Administration Route | Administration Dosage (mg · kg$^{-1}$) | Timing of Blood Sampling |
|---|---|---|---|---|
| Compound I-1 | whole blood | intravenous injection | 2.72 (equivalent to 2 mg · kg$^{-1}$ of everolimus) | 0 min, 0.0833 h, 0.25 h, 0.5 h, 1 h, 1.5 h, 2 h, 3 h, 4 h, 6 h, 8 h, 24 h. |
| Everolimus | | oral administration | 10 | |

Figure 9:
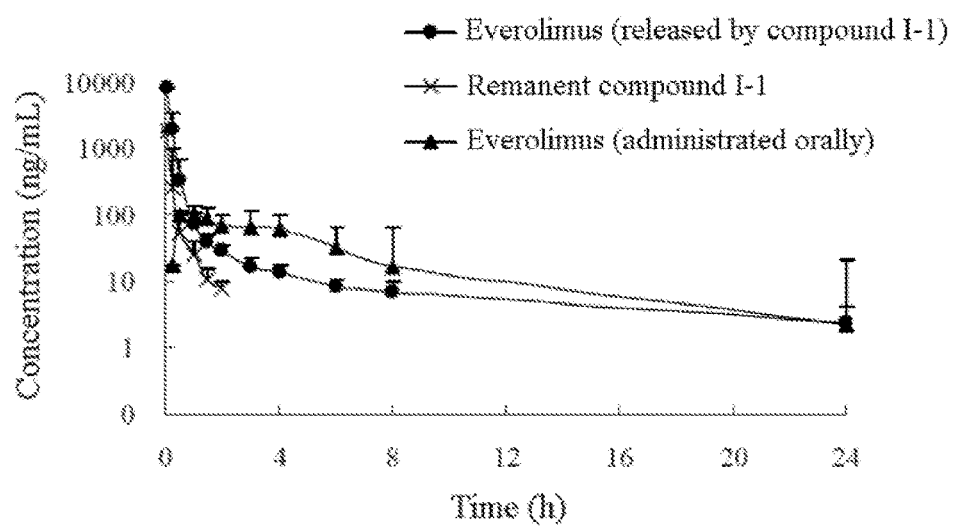
FIG. 9 is a curve plotting by average plasma concentration in SD male rats versus time.

The health condition of the animals was observed in 2 h after administration. Then the animals were observed when blood was sampled every time until the last sample was collected. The test results of the blood samples are shown in Tables 14 to 16 and FIG. 9.

TABLE 14

Concentration of everolimus in plasma after single intravenous injection administration of compound I-1 (2.72 mg · kg$^{-1}$) to male SD rats

| | Time (h) | | | | | | | | | | |
|---|---|---|---|---|---|---|---|---|---|---|---|
| | 0 | 0.0833 | 0.25 | 0.5 | 1 | 1.5 | 2 | 3 | 4 | 6 | 8 | 24 |
| Mean plasma concentration (ng/mL) | 0.0 | 8421.1 | 1995.0 | 326.1 | 73.6 | 40.4 | 28.1 | 16.9 | 13.8 | 8.1 | 6.8 | 2.3 |
| deviation (SD) | 00 | 1584.9 | 360.4 | 67.0 | 9.8 | 6.4 | 5.5 | 3.4 | 2.7 | 3.4 | 1.8 | 0.2 |

TABLE 15

Concentration of everolimus in plasma after oral administration of everolimus (10.000 mg · kg$^{-1}$) to male SD rats

| | Time (h) | | | | | | | | | | |
|---|---|---|---|---|---|---|---|---|---|---|---|
| | 0 | 0.25 | 0.5 | 1 | 1.5 | 2 | 3 | 4 | 6 | 8 | 24 |
| Mean plasma concentration (ng/mL) | 0.0 | 17.3 | 99.9 | 99.1 | 90.4 | 69.7 | 64.3 | 61.4 | 32.3 | 16.3 | 2.2 |
| deviation (SD) | 00 | 4.3 | 36.8 | 30.5 | 49.3 | 38.0 | 30.5 | 47.9 | 18.7 | 9.7 | NA |

NA: Not Available

TABLE 16

Pharmacokinetics parameters of everolimus in plasma after single intravenous injection administration of compound I-1 (2.72 mg · kg$^{-1}$) or oral administration of everolimus (10.000 mg · kg$^{-1}$), to male SD rats

| Drug | Administration Route | Dosage (mg · kg$^{-1}$) | $t_{1/2}$ (h) | $t_{max}$ (h) | $C_{max}$ (ng/mL) | AUC$_{0\to t}$ (h * ng/mL) | AUC$_{0\to\infty}$ (h * ng/mL) | AUC Extr (%) | MRT (h) |
|---|---|---|---|---|---|---|---|---|---|
| Everolimus | PO | 10 | 2.20 | 1.91 | 125.66 | 453.59 | 454.32 | 6.90 | 3.17 |
| compound I-1 (everolimus in plasma) | IV | 2.72 | 2.3 | 0.083 | 8421.1 | 2488.16 | 2506.49 | 0.76 | 0.37 |

Note:
MRT represents mean residence time

From the above Table 14 to Table 16 and the plasma concentration-time curve (FIG. 9), rats administrated with 10 mg/Kg of everolimus orally show a relative low average plasma concentration. But for rats injected with compound I-1 in a dosage equivalent to one fifth of that of everolimus administrated orally (2 mg/Kg), the mean plasma concentration of everolium released in rats is much higher than that released by everolium orally administrated. The area under the curve (AUC) plotted by plasma concentration of everolimus released in the rats injected with 2.72 mg/Kg of compound I-1 (equivalent to 2 mg/Kg of everolimus), vs. time is about 2500; while the area under the curve plotted by plasma concentration of everolimus in the rats orally administrated with everolimus, vs. time is merely about 450. Thus, in the case of injecting compound I-1 in a dosage of one fifth of that of everolimus via oral administration, the bioavailability of everolimus released in vivo by the injected compound I-1 is 5 to 6 times to that by orally administrated everolimus.

Conclusion: the bioavailability of everolimus administrated orally is extremely low, but compound I-1 administrated via injection can completely release a considerable amount of everolimus. Thus the problem that the bioavailability of everolimus is not high is dissolved.

In summary, it is revealed based on the above study that:
1) Characteristics of rapamycin, such as a poor water solubility and an unstable chemical structure in vivo, are the main reasons for its poor bioavailability. Thus, improving the water solubility and enhancing the structural stability in vivo of rapamycin is the key point for improving its bioavailability. The rapamycin compounds modified with glutathione can significantly improve its water solubility. The compounds after modification can be well dissolved in normal saline with stable structures, and thus can be used for injection. As a result, the bioavailability of the rapamycin compounds in vivo is significantly improved.

2) The compounds after modification can gradually release the original drugs in the serum of rats. Thus, they can show a sustained-release effect and prolong the action time of drugs in vivo.

3) The in vivo and in vitro tests on animals indicate that the compounds after modification show a higher tumor inhibitory activity and a lower toxicity in vivo as compared with the original compounds.

The invention claimed is:

1. A compound of formula I or a pharmaceutically acceptable salt thereof:

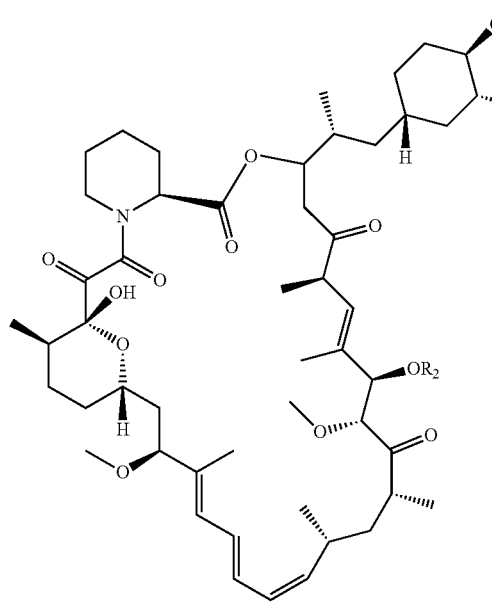

wherein,
$R_1$ is H or $R_3$;
$R_2$ is H or $R_4$—$R_5$;
and $R_1$ and $R_2$ are not simultaneously H;
$R_3$ is $R_4$—$R_5$, —$CH_2CH_2O$—$R_4$—$R_5$,

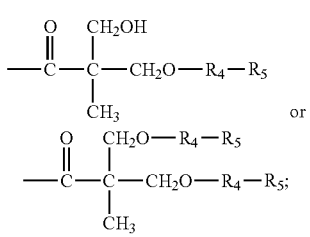

$R_4$ is

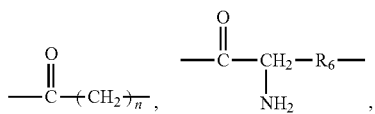

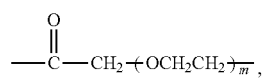

carbonyl $C_2$-$C_6$ alkenylene or carbonyl $C_2$-$C_6$ alkynylene;
n is an integer less than or equal to 6;
m is an integer less than or equal to 6;
$R_5$ is glutathionyl of formula II:

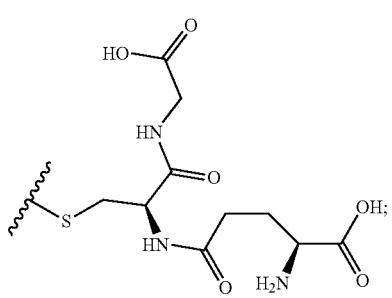

and
$R_6$ is $C_1$-$C_6$ alkylene, $C_2$-$C_6$ alkenylene or $C_2$-$C_6$ alkynylene.

2. The compound according to claim 1, wherein $R_3$ is $R_4$—$R_5$ or —$CH_2CH_2O$—$R_4$—$R_5$.

3. The compound according to claim 1, wherein $R_4$ is

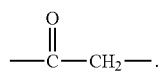

4. The compound according to claim 1, wherein, $R_1$ is —$CH_2CH_2O$—$R_4$—$R_5$.

5. The compound according to claim 4, wherein, $R_4$ is

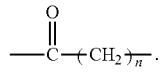

6. The compound according to claim 4, wherein, $R_2$ is H.

7. The compound according to claim 1, wherein the compound of formula I is selected from:

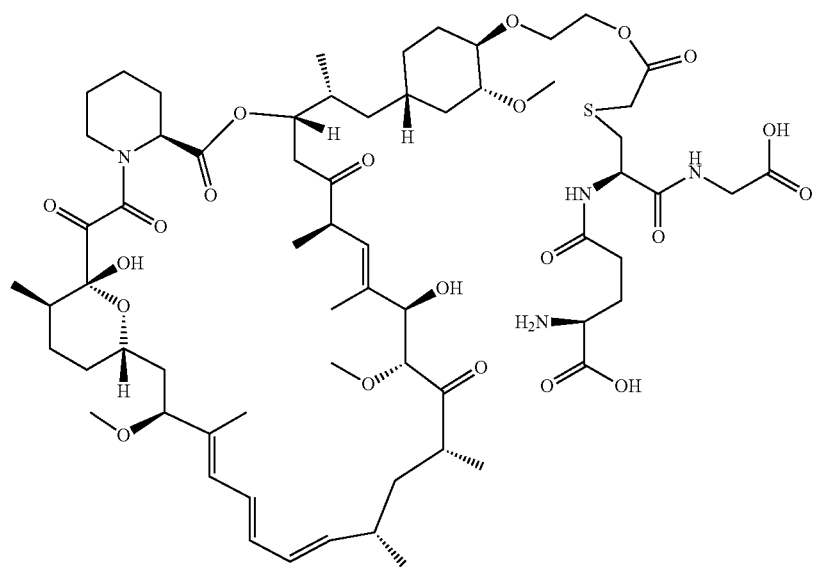
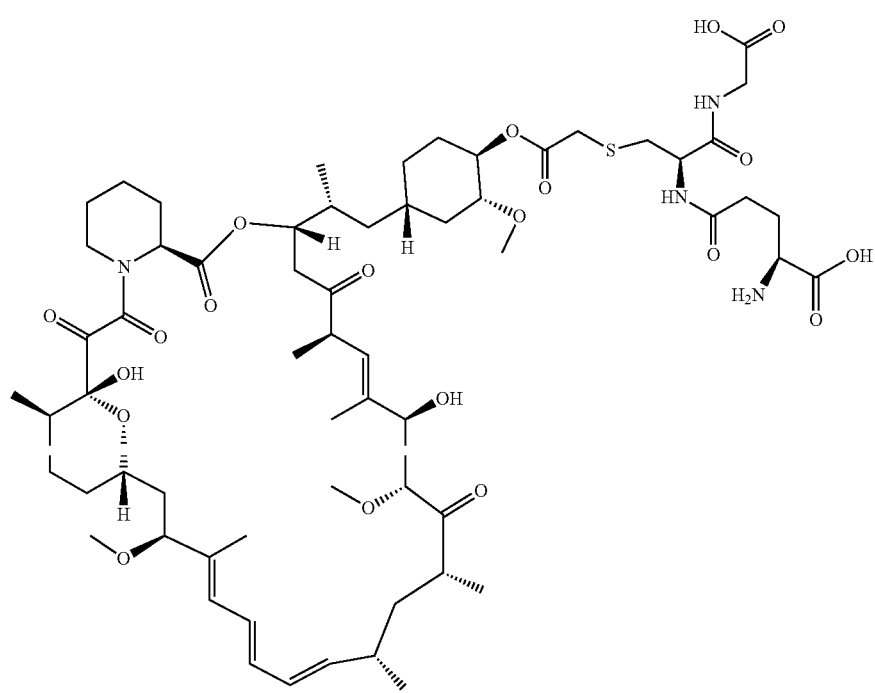

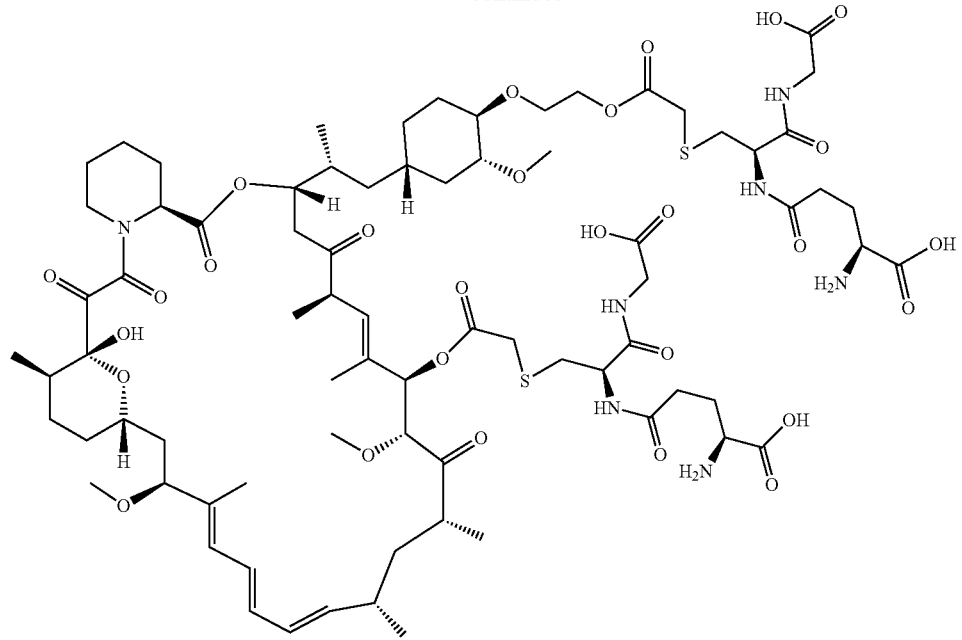
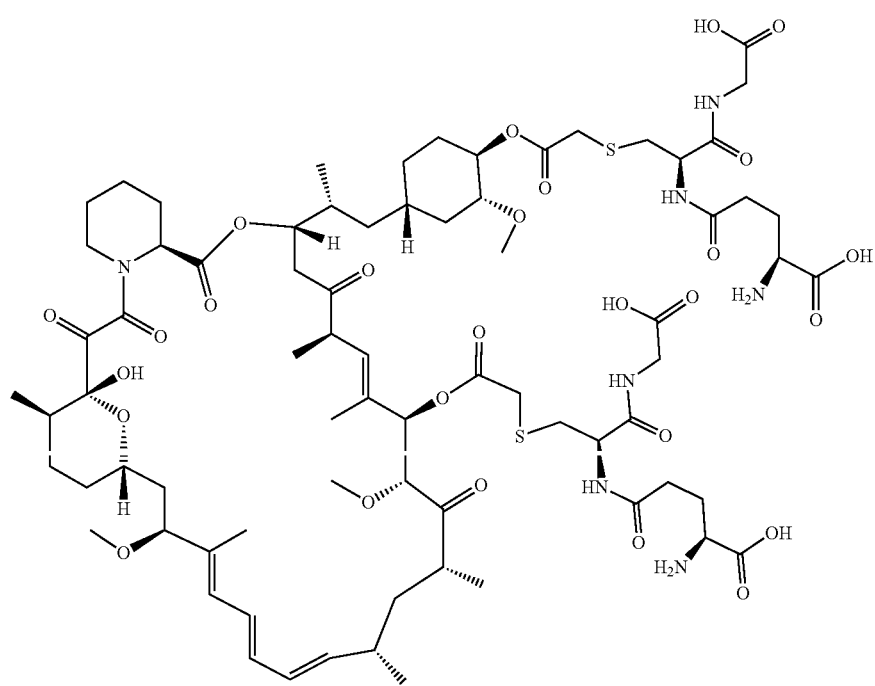

-continued
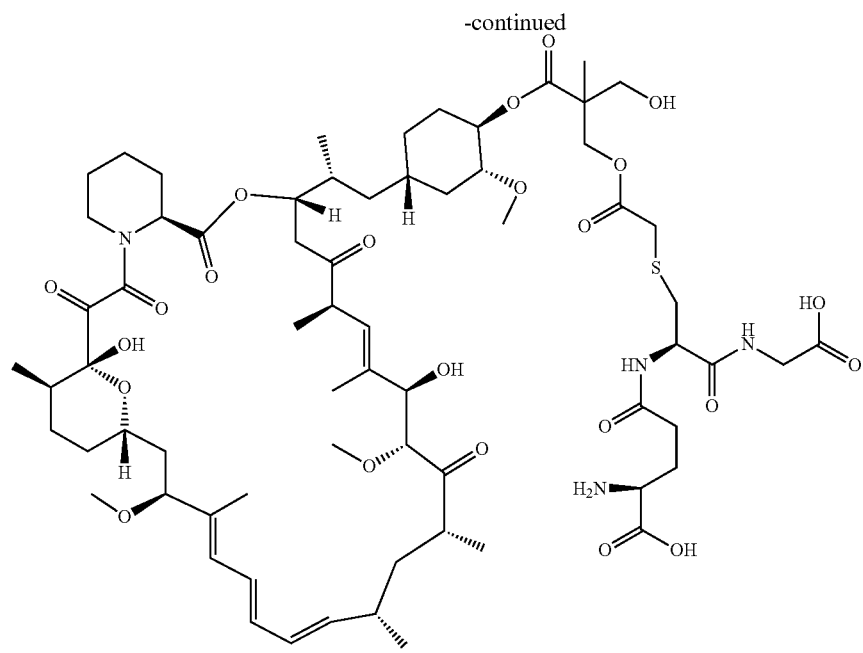
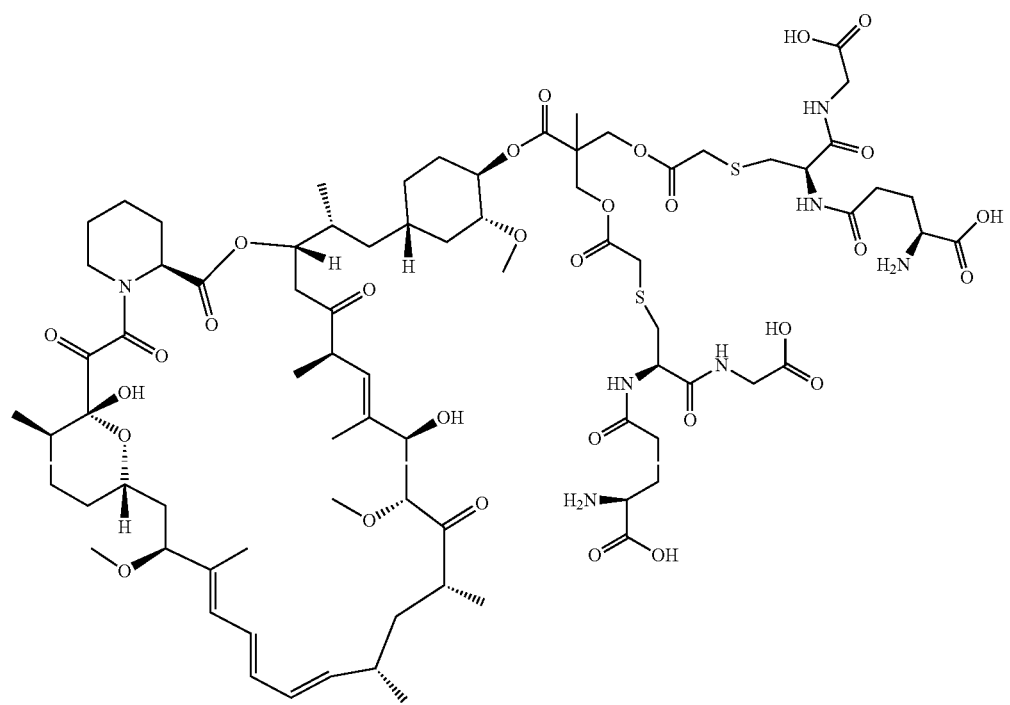

-continued

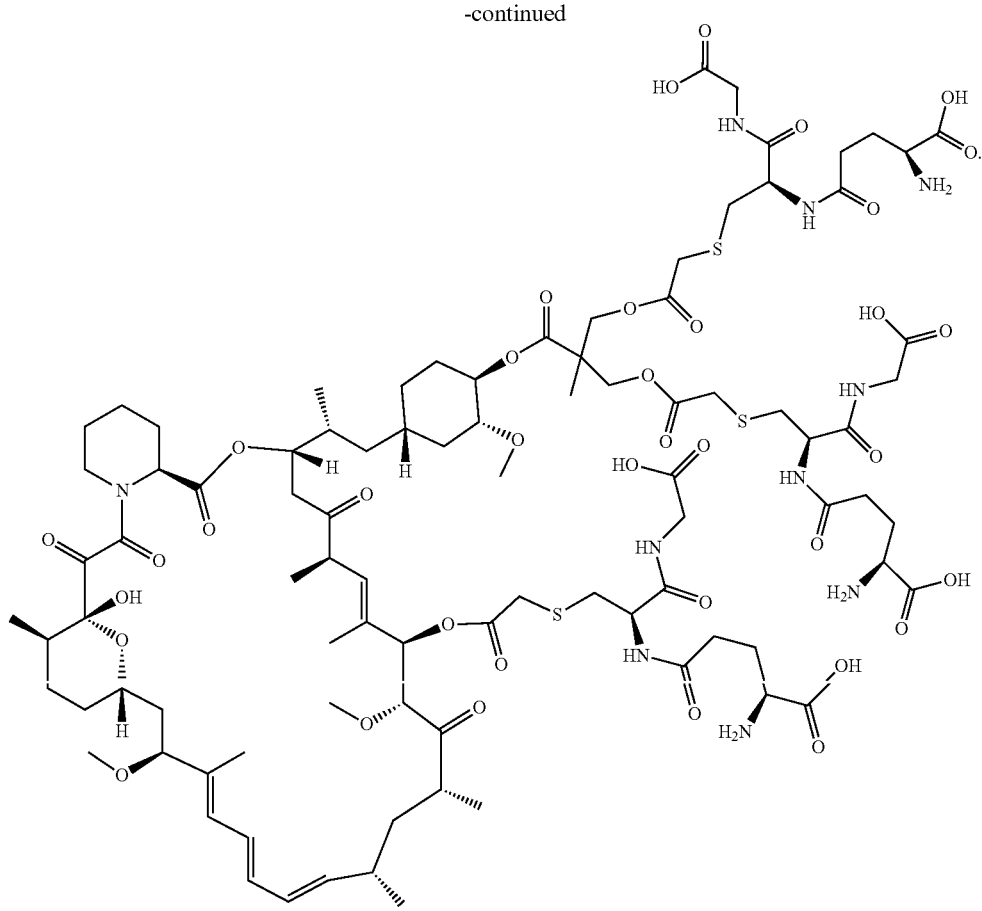

8. A pharmaceutical composition comprising an effective amount of the compound of formula I or a pharmaceutically acceptable salt thereof according to claim 1; and pharmaceutical adjuvants comprising pharmaceutical carriers, excipients or combinations thereof.

9. A formulation comprising the compound or a pharmaceutical acceptable salt thereof according) A formulation comprising the pharmaceutical composition according to claim 8, wherein the formulation is a tablet, capsule, injection, powder, granule, drug eluting stent, pill or film.

10. The formulation according to claim 9, wherein the formulation is an injection, with water for injection as vehicle.

11. The formulation according to claim 10, wherein the injection is a lyophilized powder for injection, with normal saline as vehicle for reconstitution.

12. The pharmaceutical composition according to claim 8, wherein the compound of formula I is a citrate salt thereof.

13. A formulation comprising the compound or a pharmaceutical acceptable salt thereof according to claim 1, wherein the formulation is a tablet, capsule, injection, powder, granule, drug eluting stent, pill or film.

14. The formulation according to claim 13, wherein the formulation is an injection, with water for injection as vehicle.

15. The formulation according to claim 14, wherein the injection is a lyophilized powder for injection, with normal saline as vehicle for reconstitution.

16. A process for preparing a compound of formula I according to claim 1 comprising the steps of:

(a) reacting a compound of formula III with $XR_{10}COOH$ so as to obtain a compound of formula IV:

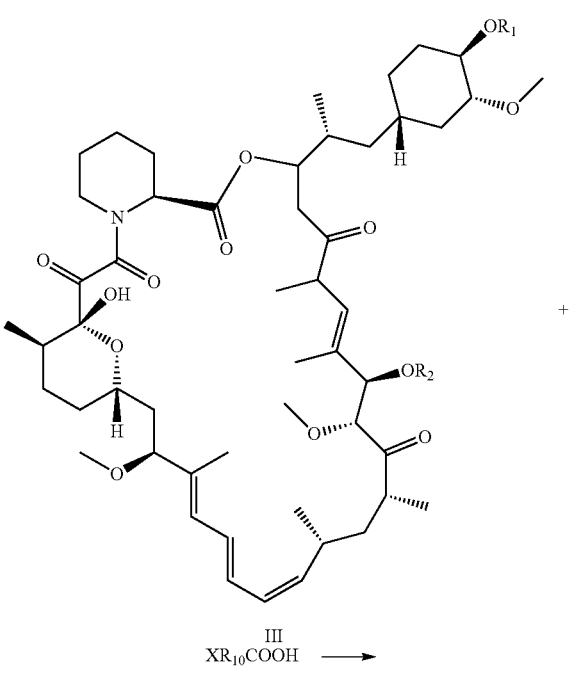

-continued

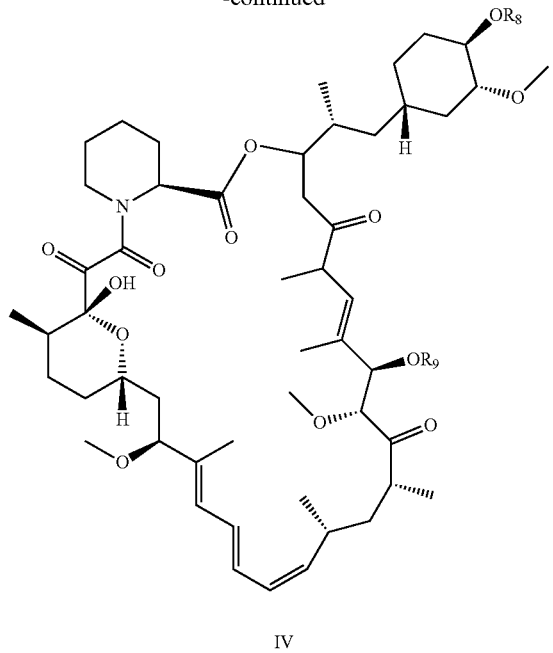

IV wherein,

R₇ is H, —CH₂CH₂OH or

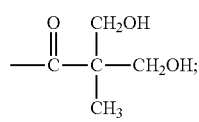

R₈ is H, R₄X, —CH₂CH₂OR₄X,

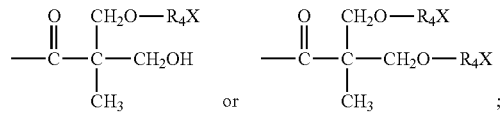

R₉ is H or R₄X;

and R₈ and R₉ are not simultaneously H;

R₁₀ is C₁-C₆ alkylene,

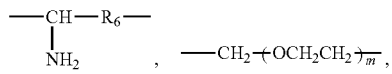

C₂-C₆ alkenylene or C₂-C₆ alkynylene; and

X is a halogen atom;

(b) reacting the compound of formula IV obtained from step (a) with a polypeptide, so as to obtain the compound of formula I:

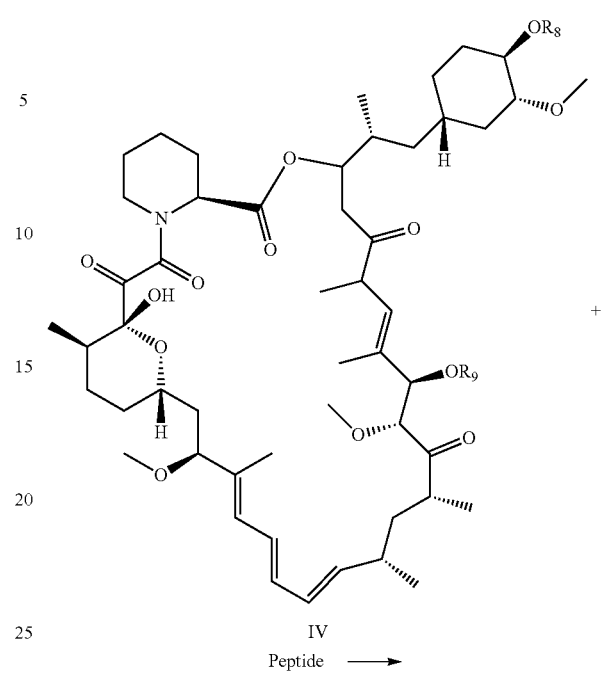

IV
Peptide ⟶

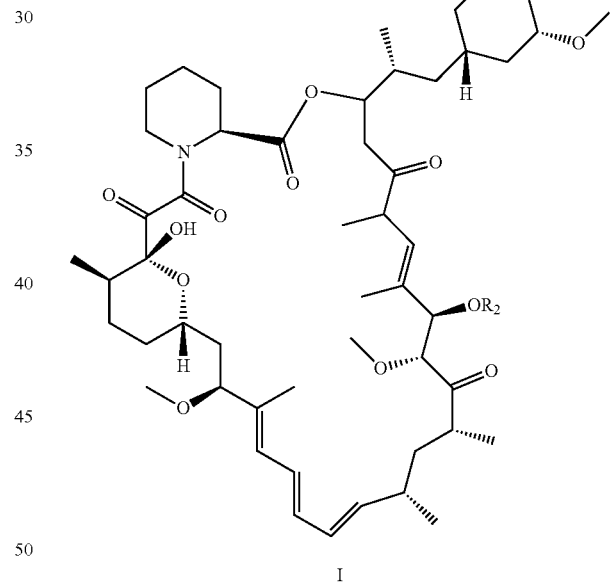

I wherein,

R₁ is H or R₃;

R₂ is H or R₄—R₅;

and R₁ and R₂ are not simultaneously H;

R₃ is R₄—R₅, —CH₂CH₂O—R₄—R₅,

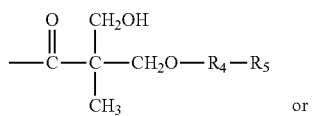
or

-continued

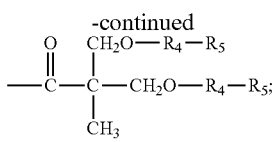

R$_4$ is

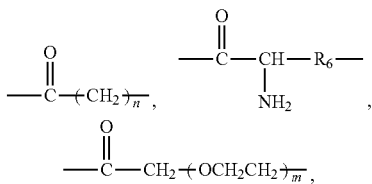

carbonyl C$_2$-C$_6$ alkenylene or carbonyl C$_2$-C$_6$ alkynylene;
n is an integer less than or equal to 6,
m is an integer less than or equal to 6,
R$_5$ is glutathionyl of formula II:

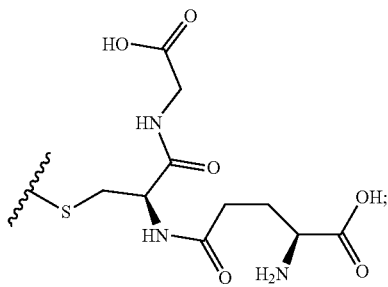

and
R$_6$ is C$_1$-C$_6$ alkylene, C$_2$-C$_6$ alkenylene or C$_2$-C$_6$ alkynylene.

17. The process according to claim 16, wherein in step (b), the reaction of compound of formula IV and the polypeptide is carried out in a mixed solvent, which is a N,N-dimethylformamide-alcohol-water mixed solvent.

18. The process according to claim 17, wherein in the mixed solvent, the ratio of N,N-dimethylformamide-alcohol-water is 1:(1-5):(1:5) by volume.

19. The process according to claim 18, wherein in the mixed solvent, the ratio of N,N-dimethylformamide-alcohol-water is 1:2:1 by volume.

20. The process according to claim 17, wherein in step (b), the reaction of compound of formula IV and the polypeptide is carried out in a N,N-dimethylformamide-ethanol-water mixed solvent.

21. The process according to claim 16, wherein X is I or Br atom.

22. A method of treating or inhibiting transplant rejection comprising administering to a patient in need thereof a pharmaceutically effective amount of the compound or a pharmaceutical acceptable salt thereof according to claim 1.

23. The method according to claim 22, wherein the administration is by injection of the pharmaceutically effective amount of the compound or a pharmaceutical acceptable salt thereof according to claim 1 once weekly.

24. A method of treating tumor, fungal infection or vascular disease comprising administering to a patient in need thereof a pharmaceutically effective amount of the compound or a pharmaceutical acceptable salt thereof according to claim 1.

25. The method according to claim 24, wherein the tumor is selected from renal cell carcinoma, renal epithelial renal cell carcinoma, breast cancer, pancreatic cancer, lung cancer, prostate cancer, subependymal giant cell astrocytoma, or renal angiomyolipoma.

26. A method of treating or inhibiting transplant rejection comprising administering to a patient in need thereof a pharmaceutically effective amount of the pharmaceutical composition according to claim 8.

27. The method according to claim 26, wherein the administrating is by injection of the pharmaceutically effective amount of the pharmaceutical composition according to claim 8 once weekly.

28. A method of treating tumor, fungal infection or vascular disease comprising administering to a patient in need thereof a pharmaceutically effective amount of the pharmaceutical composition according to claim 8.

29. The method according to claim 28, wherein the tumor is selected from renal cell carcinoma, renal epithelial renal cell carcinoma, breast cancer, pancreatic cancer, lung cancer, prostate cancer, subependymal giant cell astrocytoma, or renal angiomyolipoma.

* * * * *